(12) United States Patent
Hermalyn et al.

(10) Patent No.: US 11,774,349 B2
(45) Date of Patent: Oct. 3, 2023

(54) SYSTEMS AND METHODS FOR MEASURING EMISSIONS FROM A BUILDING

(71) Applicant: Thalo Labs, Inc., Brooklyn, NY (US)

(72) Inventors: Brendan Hermalyn, Milford, CT (US); John Kolaczynski, Brooklyn, NY (US); Samuel Patterson, Brooklyn, NY (US); Mihir Juvvadi, Brooklyn, NY (US); Thomas Evenat, Brooklyn, NY (US)

(73) Assignee: Thalo Labs, Inc., Brooklyn, NY (US)

( * ) Notice: Subject to any disclaimer, the term of this patent is extended or adjusted under 35 U.S.C. 154(b) by 0 days.

(21) Appl. No.: 18/174,411

(22) Filed: Feb. 24, 2023

(65) Prior Publication Data

US 2023/0266235 A1    Aug. 24, 2023

Related U.S. Application Data

(60) Provisional application No. 63/313,678, filed on Feb. 24, 2022.

(51) Int. Cl.
*G01N 21/31*     (2006.01)
*G06Q 30/018*    (2023.01)
*G01N 33/00*     (2006.01)

(52) U.S. Cl.
CPC ......... *G01N 21/31* (2013.01); *G01N 33/0004* (2013.01); *G01N 33/0027* (2013.01); *G06Q 30/018* (2013.01)

(58) Field of Classification Search
CPC ............... G01N 33/0027; G01N 21/31; G01N 33/0004; Y02W 90/00
See application file for complete search history.

(56) References Cited

U.S. PATENT DOCUMENTS

| 10,962,437 B1 | 3/2021 | Nottrott et al. |
| 2008/0195329 A1 | 8/2008 | Prince et al. |
| 2010/0198736 A1* | 8/2010 | Marino ............ G06Q 40/04 |
| | | 705/308 |

FOREIGN PATENT DOCUMENTS

| CA | 2 707 254 A1 | 9/2010 | |
| CN | 107179289 B * | 5/2018 | ......... G01N 21/3504 |

(Continued)

OTHER PUBLICATIONS

Hellwing et al., "Technical note: Test of a low-cost and animal-friendly system for measuring methane emissions from dairy cows", Journal of Dairy Science, vol. 95, No. 10, Oct. 2012, pp. 6077-6085.

(Continued)

*Primary Examiner* — Maurice C Smith
(74) *Attorney, Agent, or Firm* — McDonnell Boehnen Hulbert & Berghoff LLP

(57) ABSTRACT

An example system for measuring emissions from a building includes a housing, a plurality of sensors arranged in the housing to detect concentrations of gas constituents in gas exiting the building, a gas flow sensor to detect a gas flow rate of the gas exiting the building, and a computing device to perform functions of calculating a total emissions of the particular gas constituent being tracked from a concentration of the particular gas constituent detected by the plurality of sensors and the gas flow rate, calculating an emission rate of the particular gas constituent being tracking, determining whether the total emissions and the emission rate of the particular gas constituent are within acceptable ranges, and based on the total emissions and the emission rate of the particular gas constituent being outside the acceptable ranges, outputting a prompt to a building computer system or operator indicating an alert.

25 Claims, 11 Drawing Sheets

(56) References Cited

FOREIGN PATENT DOCUMENTS

| | | | |
|---|---|---|---|
| CN | 113713536 A | * | 11/2021 |
| CN | 113916616 A | * | 1/2022 |
| EP | 1 306 769 A2 | | 5/2003 |

OTHER PUBLICATIONS

Wathes et al., "Concentrations and emission rates of aerial ammonia, nitrous oxide, methane, carbon dioxide, dust and endotoxin in UK broiler and layer houses", British Poultry Science, vol. 38, No. 1, Mar. 1997, pp. 14-28.

International Search Report and Written Opinion prepared by the European Patent Office in International Application No. PCT/US23/063244, dated May 11, 2023.

* cited by examiner

SYSTEMS AND METHODS FOR MEASURING EMISSIONS FROM A BUILDING

CROSS REFERENCE TO RELATED APPLICATION

This application claims priority to U.S. Application No. 63/313,678, filed on Feb. 24, 2022, the entire contents of which are herein incorporated by reference.

FIELD

The disclosure relates generally to building emissions monitoring or measuring, and more particularly to, a new and useful system for directly measuring emissions from a building for asset level emissions monitoring via detection of concentrations of gas constituents in gas exiting the building.

BACKGROUND

Buildings are a large consumer of energy and therefore a large source of greenhouse gas emissions, both direct ("scope 1") from onsite combustion and indirect ("scope 2") from use of electricity generated elsewhere. Example direct emissions associated with operating buildings have several sources. Dominant sources include combustion of fossil fuels (e.g., such as coal, natural gas, oil) for generation of electricity, heat, steam, and power generation that result in release of carbon dioxide, methane, and nitrous oxide. Additionally, leakage or incomplete combustion of fossil fuels can contribute substantially to the direct emissions.

Several frameworks and tools exist for estimating emissions of a building. An emission factor is a representative value that attempts to relate a quantity of a pollutant released to the atmosphere with an activity associated with the release of that pollutant. Emission factors are usually expressed as a weight of pollutant divided by a unit weight, volume, distance, or duration of the activity emitting the pollutant. Such factors facilitate estimation of emissions from various sources of air pollution. In most cases, these factors are simply averages of all available data of acceptable quality, and are generally assumed representative of long-term averages for all facilities in a source category.

SUMMARY

Example systems and methods described herein enable directly measuring emissions of various gas constituents within gas, from, for example, a flue exhaust, exiting a building, in contrast to attempting to calculate an estimate using emission factors. Each building is unique, and thus, a direct measurement system provides a much more precise and accurate determination of emissions from the building than usage of area-wide emission factors. In addition, a direct measurement system offers numerous further advantages for identifying operation issues, leaks or incomplete combustion, predicting maintenance needs, and other benefits customized for the building.

In one example, a system for measuring emissions from a building is described comprising a housing, and a plurality of sensors arranged in the housing to detect concentrations of gas constituents in gas exiting the building either directly or indirectly, and the concentrations of gas constituents include a particular gas constituent being tracked, and the plurality of sensors are in a first pathway of the gas exiting the building. The system also comprises a gas flow sensor to detect a gas flow rate of the gas exiting the building and the gas flow sensor is in a second pathway of the gas exiting the building, and a computing device having one or more processors to perform functions. The functions comprise calculating a total emissions of the particular gas constituent being tracked during a time period by integrating a concentration of the particular gas constituent detected by the plurality of sensors, multiplied by the gas flow rate detected by the gas flow sensor, over the time period, calculating an emission rate of the particular gas constituent being tracking during the time period by dividing the total emissions by a duration of the time period, determining whether the total emissions of the particular gas constituent and the emission rate of the particular gas constituent are within acceptable ranges, and based on the total emissions of the particular gas constituent and the emission rate of the particular gas constituent being outside the acceptable ranges, outputting a prompt to a building computer system indicating an alert.

In another example, a method for measuring emissions from a building is described comprising detecting, via a plurality of sensors arranged in a housing, concentrations of gas constituents in gas exiting the building, and the concentrations of gas constituents include a particular gas constituent being tracked, and the plurality of sensors are in a first pathway of the gas exiting the building. The method also may comprise detecting, via a gas flow sensor, a gas flow rate of the gas exiting the building, and the gas flow sensor is in a second pathway of the gas exiting the building. The method also comprises calculating, by a computing device having one or more processors, a total emissions of a particular gas constituent being tracked during a time period by integrating a concentration of the particular gas constituent, multiplied by the gas flow rate detected by the gas flow sensor, over the time period, calculating, by the computing device, an emission rate of the particular gas constituent being tracked during the time period by dividing the total emissions by a duration of the time period, determining whether the total emissions of the particular gas constituent and the emission rate of the particular gas constituent are within acceptable ranges, and based on the total emissions of the particular gas constituent and the emission rate of the particular gas constituent being outside the acceptable ranges, outputting a prompt to a building computer system indicating an alert.

The features, functions, and advantages that have been discussed can be achieved independently in various examples or may be combined in yet other examples. Further details of the examples can be seen with reference to the following description and drawings.

BRIEF DESCRIPTION OF THE FIGURES

Examples, objectives and descriptions of the present disclosure will be readily understood by reference to the following detailed description of illustrative examples when read in conjunction with the accompanying drawings, wherein.

DESCRIPTION OF THE EMBODIMENTS

Figure 1:
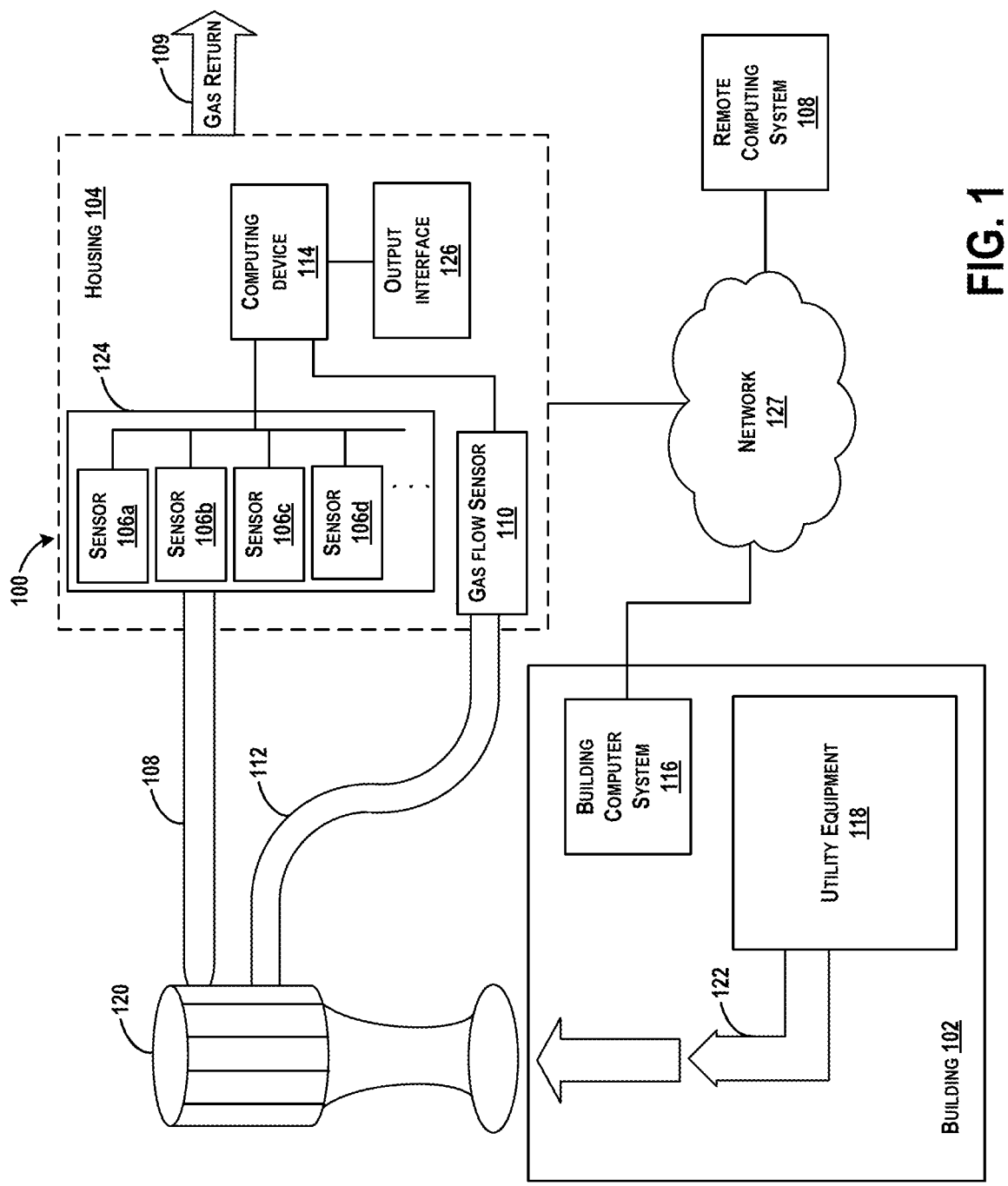
FIG. 1 illustrates a system 100 for measuring emissions from a building, according to an example implementation.

Disclosed examples will now be described more fully hereinafter with reference to the accompanying drawings. Several different examples are described and should not be construed as limited to all possible alternatives. Rather, these examples are described so that this disclosure is thorough and complete and fully conveys a scope of the disclosure to those skilled in the art.

Within examples herein, in operation, systems are used to perform functions for detecting and tracking gas flow rate or flux and gas constituents of gas exiting a unit volume (e.g., such as an exhaust stack or a combustion analysis port of an exhaust stream), such as resulting from combustion of natural gas, methane, coal, oil, or diesel fuel in a water heater, boiler, or heating and ventilation system within a building. In particular, example systems are configured to seat over or to connect to an outlet of the exhaust stack, track gas flow rate out of the exhaust stack, track concentrations of a set of gas constituents in gas exiting the exhaust stack and therefore output by one or more utility systems servicing the building, and to transmit resulting data to a remote computer system. In one example, the remote computer system is operable to then process the data through a machine learning-driven recommendation engine to identify total emissions from these utility systems (or from the building more generally) over a time period; derive a baseline emission condition for the building; characterize excess emissions from the building based on the baseline emissions condition; predict maintenance or adjustments to utility systems in the building to reduce emissions to the baseline emissions condition; compile these data into actionable insights; trigger alarms; and present these actionable insights to the building computer system 116 to guide emissions reduction and energy efficient improvement for the building.

In some examples, the system temporarily or permanently installs on a roof of a building to track emissions from an exhaust stack on the building. The remote computer system accesses emissions data captured by the system, such as streamed or broadcast intermittently by the system; estimates true energy consumption and true energy need for the building per unit time (e.g., per day, per week) based on concentrations of various gas constituents and gas flow rate detected by the system and based on known chemical conversions between fuel, thermal energy, and gas constituents for a fuel type consumed in the building); predicts a baseline fuel consumption by the building per unit time if combustion efficiency within the building were improved to a nominal standard (e.g., 90% for a heating system more than 20 years of age; 94% for a heating system less than five years of age); predicts a baseline emission condition from the building per unit time based on the known chemical conversion for the fuel and given the baseline fuel consumption per unit time at the nominal combustion efficiency; compares to standard "bottoms up" estimates of greenhouse gas emission as a report to EPA's Energy Star Portfolio Manager; predicts maintenance or an action related to a utility system in the building to improve combustion efficiency and reduce emissions down to the baseline emission condition per unit time (under similar load conditions); and then either prompts a user affiliated with the building or directly drives a building management system to perform this maintenance or action.

In some examples, a combustion system might have provisions for reducing emissions post combustion, such as a desulphurization unit or a carbon dioxide capture system. In these examples, the measurement system described herein provides a direct measurement of actual emissions post combustion and emissions remediation, which would be impossible with estimation from emissions factors alone.

Thus, the system and the remote computer system cooperate to derive an accurate baseline emissions condition for the building, based on true emissions conditions from the building, in place of a generic "emissions factor" for buildings exhibiting certain generic characteristics. Furthermore, because the system monitors true emissions from the building, the remote computer system is operable to: predict need for and specific types of maintenance to reduce emissions (e.g., total effective carbon dioxide emissions) from the building and improve energy efficiency at the building; and return prompts for such maintenance to a user affiliated with building, which may be more effective, more actionable for the user, less expensive for the building, and less environmentally-harmful than mere purchase of carbon offset credits based on a generic emissions factor for the building and energy use in the building.

As described below, within some examples, the system includes a number of components such as a main component including a sensor manifold, power electronics, sensing electronics, human-machine interface (HMI), cell/Wi-Fi antennas, and pump. In some examples, the system further includes a sub-component such as an exhaust conditioning unit that includes an electric heat exchange system to remove moisture from exhaust gas to prevent any condensation build up in the main component. The exhaust conditioning unit also has plumbing components to remove the moisture and prevent air from entering the system.

Referring now to the figures, FIG. 1 illustrates a system 100 for measuring emissions from a building 102, according to an example implementation. The system 100 includes a housing 104, and a plurality of sensors 106a-d arranged in the housing 104 to detect concentrations of gas constituents in gas exiting the building 102. The concentrations of gas constituents include a particular gas constituent being tracked, and the plurality of sensors 106a-d are in a first pathway 108 of the gas exiting the building 102. The system 100 also includes a gas flow sensor 110 to detect a gas flow rate of the gas exiting the building 102, and the gas flow sensor 110 is in a second pathway 112 of the gas exiting the building 102. The system 100 also includes a computing device 114, having one or more processors, to perform functions of calculating a total emissions of the particular gas constituent being tracked during a time period by integrating a concentration of the particular gas constituent detected by the plurality of sensors 106a-d, multiplied by the gas flow rate detected by the gas flow sensor 110, over the time period, calculating an emission rate of the particular gas constituent being tracking during the time period by dividing the total emissions by a duration of the time period, determining whether the total emissions of the particular gas constituent and the emission rate of the particular gas constituent are within acceptable ranges, and based on the total emissions of the particular gas constituent and the emission rate of the particular gas constituent being outside the acceptable ranges, outputting a prompt to a building computer system 116 indicating an alert.

In the example shown in FIG. 1, the building includes utility equipment 118, which during operation, generates emissions of gases that are directed out of the building 102 through an exhaust stack 120. The exhaust stack 120 can be positioned on a roof of the building 102 or another exterior portion of the building 102.

The system 100 is able to directly monitor emissions from the building 102 (in contrast to estimating emissions) by locating the housing 104 near or on a source of greenhouse gas emissions. In the example shown in FIG. 1, the housing 104 is positioned proximate the exhaust stack 120, such as on the roof of the building, and gas existing the exhaust 120 is provided to the housing 104 through the first pathway 108 and the second pathway 112. The first pathway 108 and the second pathway 112 include plastic tubes or flexible hoses, for example, that fluidly couple gas exiting the building 102 (or exiting the utility equipment 108) with the sensors 106a-d and the gas flow sensor 110, respectively. In another example, however, the housing 104 is positioned at or proximate to an exhaust 122 of the utility equipment 118 inside the building 102 from which gas can be sampled (e.g., drawn from a combustion analysis port on a boiler into the housing 104 using a pump).

The housing 104 is a watertight sealed housing, and the system 100 is shown to include the sensors 106a-d arranged in sensor manifold 124 within the housing 104. The sensors 106a-d are thus positioned in close proximity to minimize a volume of gas needed for sampling. A reduced gas volume also minimizes a response time of the sensors 106a-d from any event that causes a change in composition of the gas stream. Although four sensors are shown in FIG. 1, more or fewer sensors can be included. In addition, in other examples, a single sensor capable of detecting concentrations of multiple different types of gases is used.

Following sampling of the gas by the sensors 106a-d, the gas is provided through a gas return pathway 109 back to the exhaust stack 120.

The sensors 106a-d detect concentrations of a set of greenhouse gas constituents, the sensors 106a-d take the form of gas sensors to detect concentrations of gas constituents including carbon dioxide, formaldehyde (e.g., product of incomplete combustion of a fuel source), carbon monoxide, particulate matter (e.g., a product of burning coal or diesel fuel), sulfur oxide, nitrogen oxide, methane, and oxygen. In other examples, the sensors 106a-d also include one or more of a temperature sensor, a humidity sensor, a pressure sensor, and additionally or alternatively a geospatial location sensor.

In yet other examples, the sensors 106a-d include a spectrometer to detect the concentrations of the gas constituents in the gas exiting the building 102 based on an intensity of detected light. In this example, the computing device 114 can run a process, including machine-learned programs, to invert the intensity of detected light to concentrations in near real time.

Within examples, the gas flow sensor 110 takes a form of one of a wire anemometer, a pitot tube, or other gas flux sensor configured to track gas flow rate through the exhaust stack 120. In one example, the gas flow sensor 110 is positioned inside the housing 104, as shown in FIG. 1. In some examples, the housing 104 further includes a pump that draws gas in from the exhaust stack 120.

In another example, the gas flow sensor 110 is coupled to a distal end of the sampling tube (e.g., the second pathway 112) and the distal end of the sampling tube is inserted into the exhaust stack 120. Thus, gas flow rate can be measured using a pitot-static instrument within the duct of the exhaust stack 120 to ensure an accurate measurement of flow velocity without diverting or influencing the existing flow.

In some examples, the gas flow sensor 110 measures the total flow in the exhaust system, either directly (such as with a hot wire anemometer physically separate from the sensor manifold 124 as shown in FIG. 1) or indirectly (such as a pitot tube system, where a system of pressure sensors and computing system calculates the flow). An example of the system of sensors can be co-located or directly measure other components of the gas flow, including but not limited to temperature, pressure, and humidity. In this example, when coupled with the measurements from the sensor manifold 124, calculation of the total mass flux of constituent gases in the emitted gases is permitted.

In still other examples, the gas flow sensor 110 is combined with the same gas intake of the sensor manifold 124 to simplify the design.

In yet further examples, the gas flow sensor 100 is omitted if exhaust characteristics are well characterized (such as for a co-generation facility) or if mass fluxes are not of interest to the measurement.

In addition, in other examples, the system 100 further includes ambient sensors, a battery to supply power to components of the system 100, and/or a solar panel or other renewable source of energy such as thermoelectric power reclamation or wind power to charge the battery. This power reclamation may also or alternatively come from the thermal buoyancy of the exhaust gas itself.

The computing device 114 samples outputs of the sensors 106a-d and the gas flow sensor 110, such as at a rate of once per minute or once per hour, and stores received data in local memory. In one example, the system 100 includes an output interface 126, which can be a wired or wireless communication interface (e.g., wireless transmitter and receiver) to stream received data to a remote computer system 108. Thus, in one example, the computing device 114 is arranged in the housing 104 and samples the sensors 106a-d and the gas flow sensor 100 at a predetermined rate, calculates the total emissions and the emission rate, and intermittently transmits the total emission and the emission rate to the remote computer system 108 through the output interface 126 at a rate less than the predetermined rate.

Although the output interface 126 is shown separate from the computing device 114, in other examples, the output interface 126 is incorporated within the computing device 114. Further details are described below with reference to FIG. 7.

Thus, the computing device 114 samples the sensors 106a-d and the gas flow sensor 110 continuously or intermittently, compresses and/or stores raw sampled data locally, and intermittently broadcasts the raw data to the remote computer system 108, such as once per day. Within examples, the computing device 114 reads a time-series of data of concentrations of the set of emission gas constituents from the sensors 106a-d and a time-series of data of gas flow rates from the gas flow sensor 110 during a deployment period, and the output interface 126 takes the form of a wireless communication module configured to transmit the time-series of data of concentrations of the set of emission gas constituents and the time-series of data of gas flow rates to the remote computer system 108.

In an alternate example, the computing device 114 locally processes raw sampled data, and then transmits derived data to the remote computer system 108, such as once per day (rather than transmitting all sampled data).

In FIG. 1, the computing device 114 is positioned inside the housing 104. In another example, the computing device 114 is located separate from the housing 104, and the sensors 106a-d and the gas flow sensor 110 output to the output interface 126 (which includes a wireless communication transmitter) to transmit outputs of the sensors 106a-d and the gas flow sensor 110 to the computing device 114.

The remote computer system 108 is operable to receive the data from the system 100 including a time-series of data of concentrations of gas constituents, gas flow rates, location, and/or ambient data collected by sensors of the system 100, and then characterize emissions from the building 120 based on the received data. Example characterizations include identifying an excess condition of or paucity of a particular gas constituent in the set of emission gas constituents, interpreting a target utility modification to alter the condition of the particular gas constituent, serving a prompt for the target utility modification to a user affiliated with the building 102, or simply recording emissions data for future reporting to governing bodies such as the SEC or EPA, or external reports.

In one example, the remote computer system 108 hosts an operator portal and interfaces with a user, via the operator portal, to configure the system 100 for the building 102. Data is input into the operator portal to populate a building profile with characteristics of the building 102 and/or utility systems connected to the exhaust stack 120, such as a type of a utility system (e.g., water heater, cogen facility, boiler in a radiator network, a furnace in a forced-air network) connected to the exhaust stack 120; a fuel type consumed by the utility system; an age of the utility system; a nominal combustion efficiency of the utility system; a size of the building 102 (e.g., in square footage); an age of the building 102; a nominal or average occupancy of the building 102; a location (e.g., address, geospatial coordinate) of the building 102; Energy Star data; billing and/or usage rates and other information, and building occupancy data, etc. The remote computer system 108 is operable to also interface with the user to record similar data for other exhaust stacks and utility systems within the same building, for other buildings on the same campus, and/or for other buildings within the same building portfolio managed by the user.

In other examples, the remote computer system 108 retrieves or accesses building characteristic data in any other ways and stores the characteristics in any other format in a building profile. The remote computer system 108 is operable to be part of the system described herein or may be a component of the utility mainframe.

FIG. 1 further illustrates a network 127, and in some examples, the computing device 114 communicates data to the remote computing system 108 and/or the building computer system 116 via the network. Communications to and from the network 127 for the computing device 114, the remote computing system 108, and the building computer system 116 can be wired or wireless communications, for example.

Figure 2:
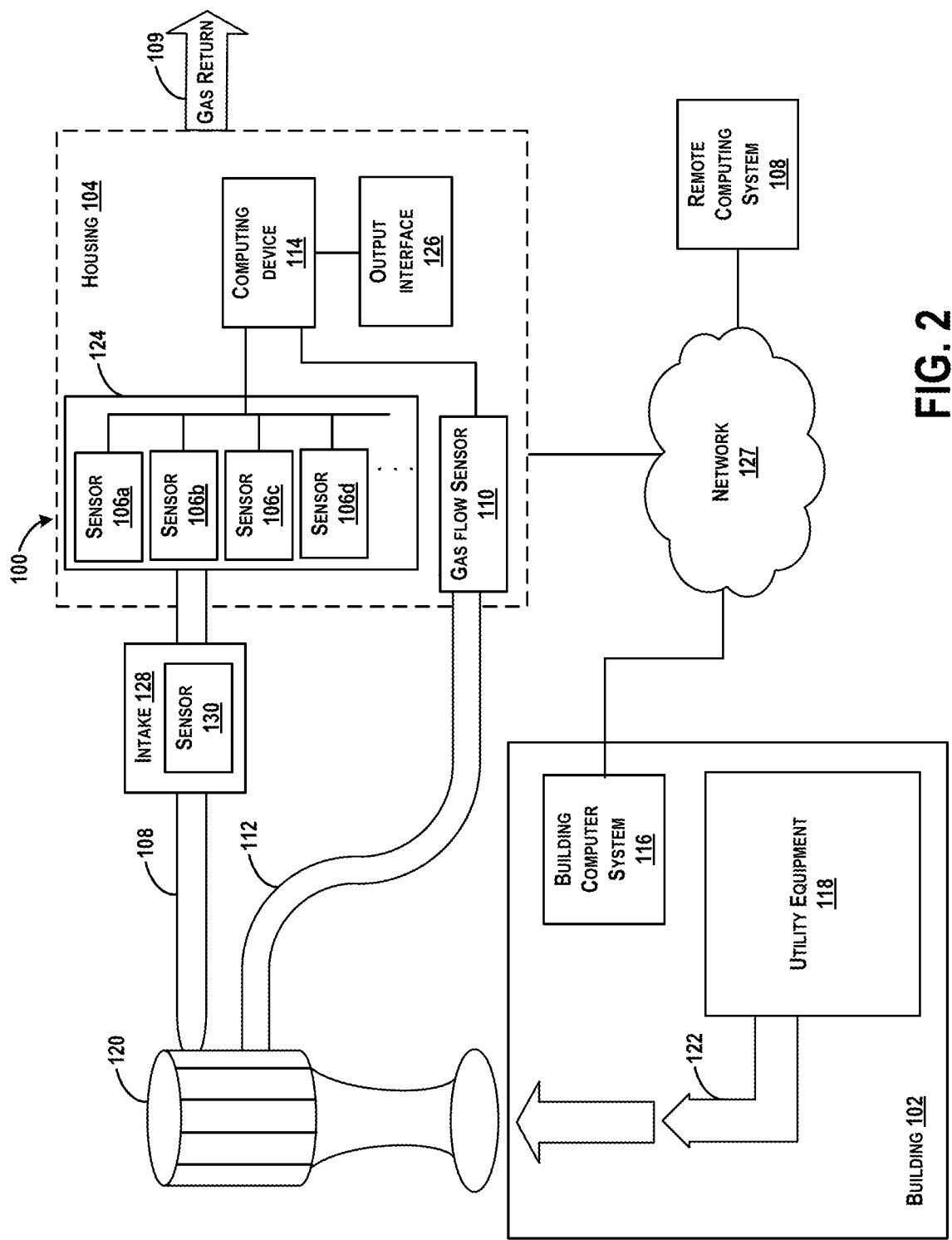
FIG. 2 illustrates another example of the system for measuring emissions from a building, according to an example implementation.

FIG. 2 illustrates another example of the system 100 for measuring emissions from a building 102, according to an example implementation. In FIG. 2, an intake 128 is provided into which an input stream of a portion of the gas exiting the building 102 passes. The intake 128 is provided within the first pathway 108, for example. In other examples, the intake 128 is provided within the second pathway 112. In still other examples, the intake 128 is coupled to the exhaust stack 120, and each of the first pathway 108 and the second pathway 112 are coupled to an output of the intake 128.

The intake 128 includes an intake sensor 130 for conditioning the input stream prior to the input stream passing through the first pathway 108. For example, the intake sensor 130 is selected from the group consisting of a dehumidifying sensor, a heater, a cooling device, a particulate filter, and a gas filter. As a specific example, the intake sensor 130 is a Peltier module that removes water or moisture from the gas exiting the exhaust stack 120, prior to the gas passing into the sensor manifold 124, so as not to damage any of the sensors 106a-d and to prevent any condensation build up in the sensor manifold 124 and provide the ability of a dry measurement of constituent gases.

In the examples shown in FIGS. 1-2, the housing 102 is positioned on a roof of the building 102 adjacent the exhaust stack 120. However, the housing 102 can be positioned at other areas inside the building as well. For instance, in one example, the housing 102 is positioned adjacent to the utility equipment 118 to measure the gas flow and gas constituents that are directly emitted from the utility equipment 118 at a combustion port.

Figure 3:
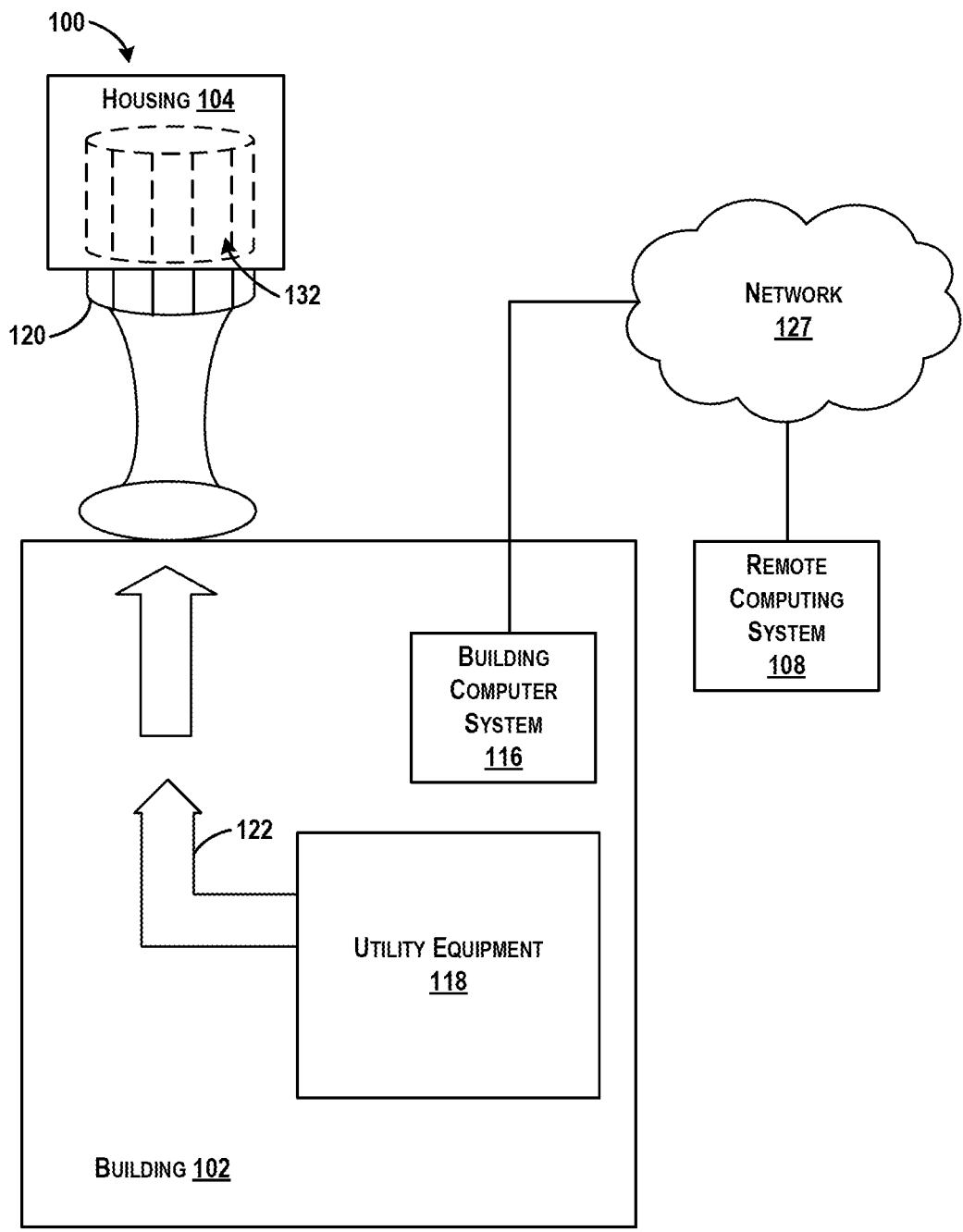
FIG. 3 illustrates another example of the system for measuring emissions from a building, according to an example implementation.

FIG. 3 illustrates another example of the system 100 for measuring emissions from a building 102, according to an example implementation. In FIG. 3, the housing 104 is configured to seat over the exhaust stack 120 of the building 102, and the sensors 106a-d and the gas flow sensor 110 are arranged in the housing 104. The housing 104 includes a set of perforations 132, on an interior surface of the housing 104 that contacts the exhaust stack 120 configured to pass the gas exiting the exhaust stack 120 to the sensors 106a-d and the gas flow sensor 110. Thus, the sensors 106a-d and the gas flow sensor 110 are positioned proximal to the perforations 132 such that the sensors 106a-d and the gas flow sensor 110 are in a pathway of the gas exiting the exhaust stack 120.

The example shown in FIG. 3, the housing defines a replacement exhaust stack cap and is configured to install on the exhaust stack 120 in replacement of a previous cap. In this implementation, all components of the housing 104 shown in FIGS. 1-2 are arranged in the housing 104.

Figure 4:
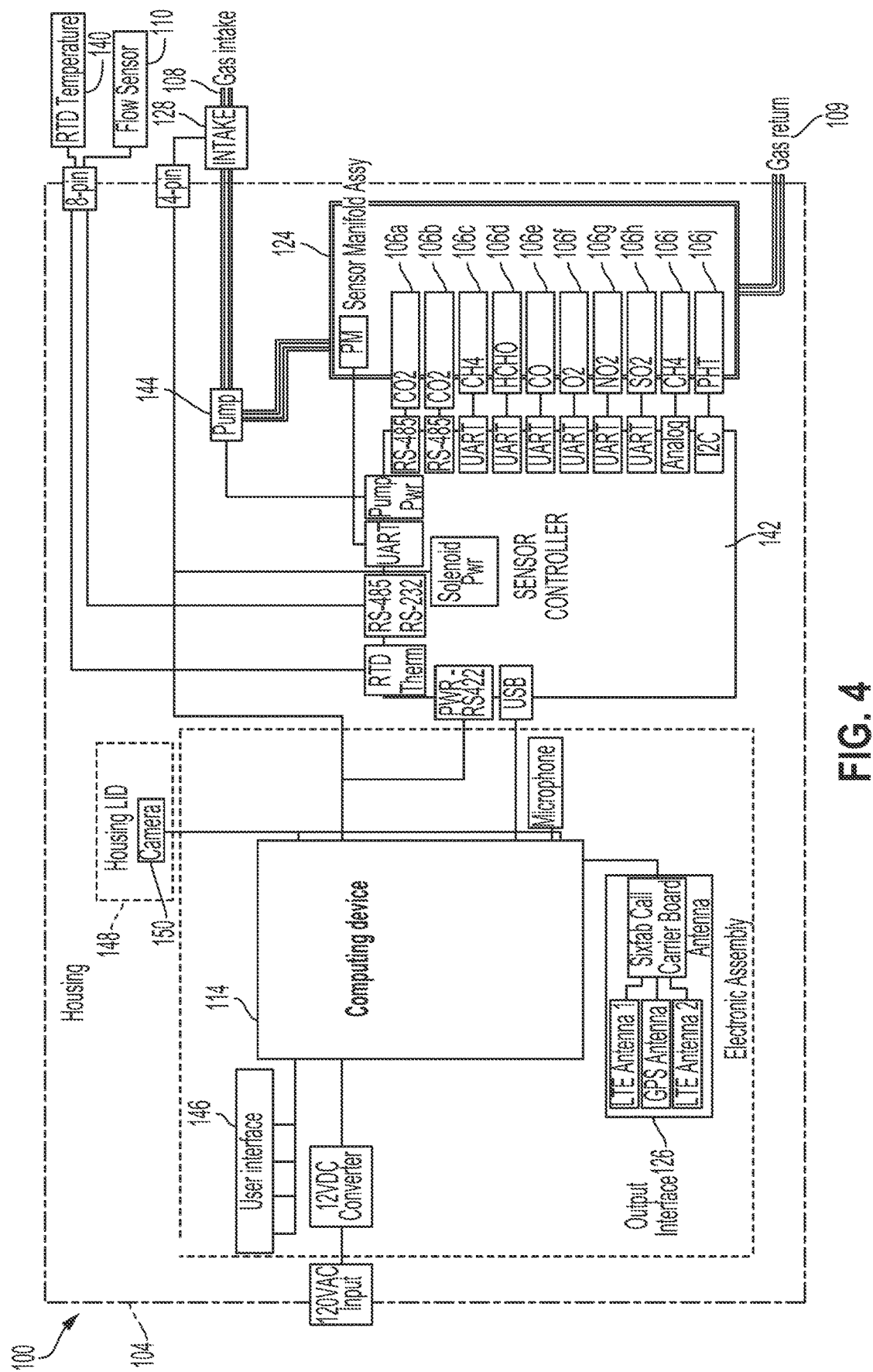
FIG. 4 illustrates another example detailed block diagram of the system, according to an example implementation.

FIG. 4 illustrates another example block diagram of the system 100, according to an example implementation. In FIG. 4, the gas flow sensor 110 and a temperature sensor 140 are exterior to the housing 104 and couple to a sensor controller 142 internal to the housing 104. The system 100 in FIG. 4 includes the sensor manifold 124, which is shown to include sensors 106a-j (e.g., $CO_2$ sensors, $CH_4$ sensors, HCHO sensor, CO sensor, O2 sensor, NO2 sensor, SO2 sensor, and a pressure-humidity-temperature (PHT) sensor). All of the sensors 106a-j output to the sensor controller 142.

The sensor controller 142 inputs raw sensor data, outputs processed data, and can control operating modes and conditions of the sensors and other components within the system 100. In some examples, the sensor controller 142 is responsible for converting and/or applying corrections to incoming sensor data prior to compute ingestion. In some examples, the sensor controller 142 will control sensing modalities and ranges dynamically based on inputs. In some examples, the sensor controller 142 will dynamically conserve sensor lifetime by cycling sensor power and gas flow inputs.

Gas from the exhaust stack 120 is pumped into the gas intake 108 with a pump 144, for example. After passing by the sensors 106a-j, the gas can be returned back to the exhaust stack via the gas return 109.

Electronics of the system 100 includes the computing device 114, the output interface 126 (e.g., shown to optionally include an antenna system with long term evolution (LTE) antennae and a global positioning system (GPS) antenna), and a user interface 146 to enable user input for providing settings and control information. The computing device 114 is in communication with the sensor controller 142 to receive the data captured by the sensors 106a-j, the gas flow sensor 110, and the temperature sensor 140 for processing.

In the example shown in FIG. 4, a configuration of the sensors 106a-j in close proximity minimizes gas volumes required and helps to ensure that all the sensors 106a-j are precisely reading the same gas flow. The pump 144 pulls a side-stream of air (e.g., about 1 liter/min) from the exhaust without overpowering any fan in the exhaust system. In addition, the intake 128 preconditions an input gas stream to remove any condensation that may occur as gas moves through the system 100. This helps to ensure that no moisture accumulates in the housing 104.

In one example, sensor accuracy is controlled through a calibration process that is completed before the system 100 is put into the field. During testing and validation stages of the system 100, calibration gases of known chemical concentrations (e.g., CO2, CH4, CO, etc.) are pumped into the sensor manifold 124, and the sensors 106a-j are calibrated against the known concentrations to ensure the system 100 will read accurately in the field.

In one example, the housing 104 takes the form of a briefcase type enclosure and includes a housing lid 148 with a camera 150. The camera 150 is used, for example, camera when in the field for operational verification. For non-exhaust systems (such as monitoring outside ambient CO2 and other weather), the camera 150 is used to track insolation, solar position, and cloud/rain cover, for example.

Figure 5A:
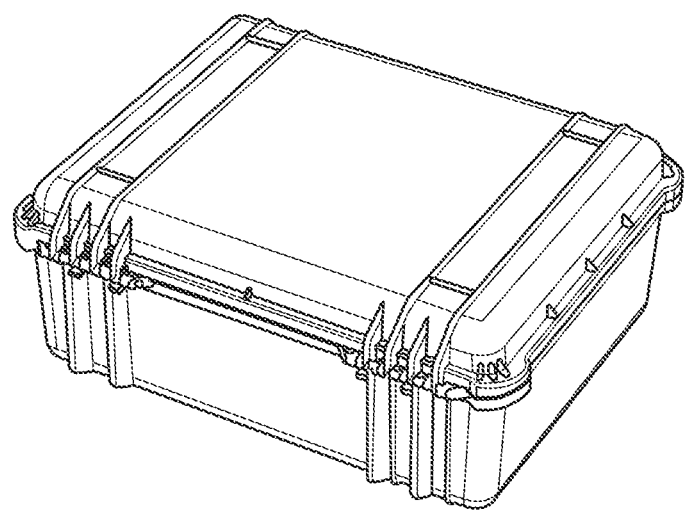
FIG. 5A is a perspective view of the housing, according to an example implementation.
Figure 5B:
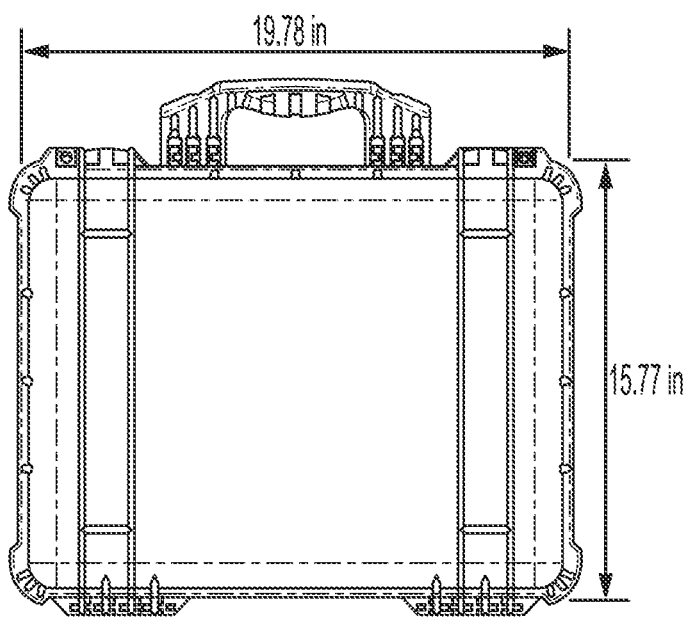
FIG. 5B is a top view of the housing, according to an example implementation.
Figure 5C:
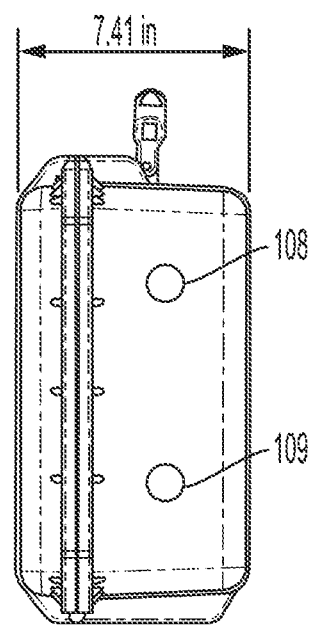
FIG. 5C is a side view of the housing, according to an example implementation.

FIG. 5A is a perspective view of the housing, according to an example implementation. FIG. 5B is a top view of the housing, according to an example implementation. FIG. 5C is a side view of the housing, according to an example implementation. As shown in FIGS. 5A-5C, the housing 104 takes the form of a briefcase type enclosure. In FIG. 5C, openings for the gas intake 108 and gas return 109 are shown. The gas intake and gas return can be positioned on any side of the housing 104 as needed, for example.

Figure 6A:
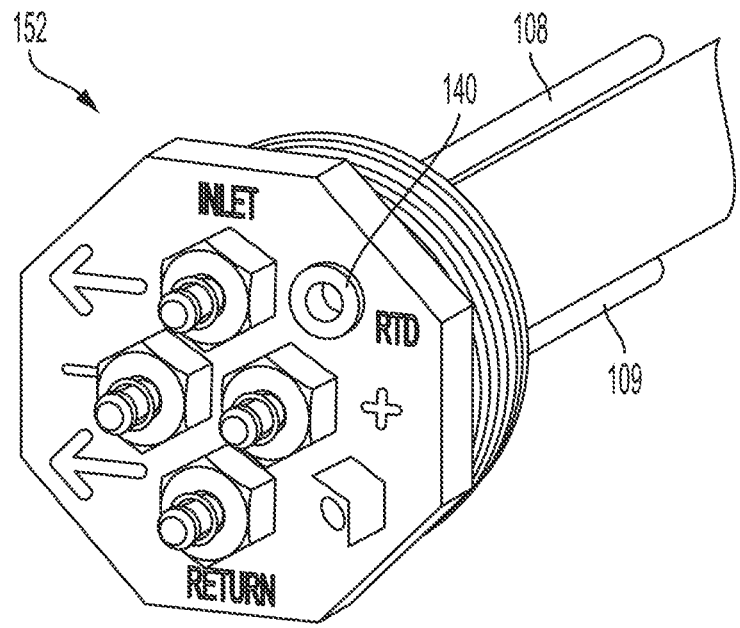
FIG. 6A illustrates a perspective view of an example gas probe for use with the system, according to an example implementation.
Figure 6B:
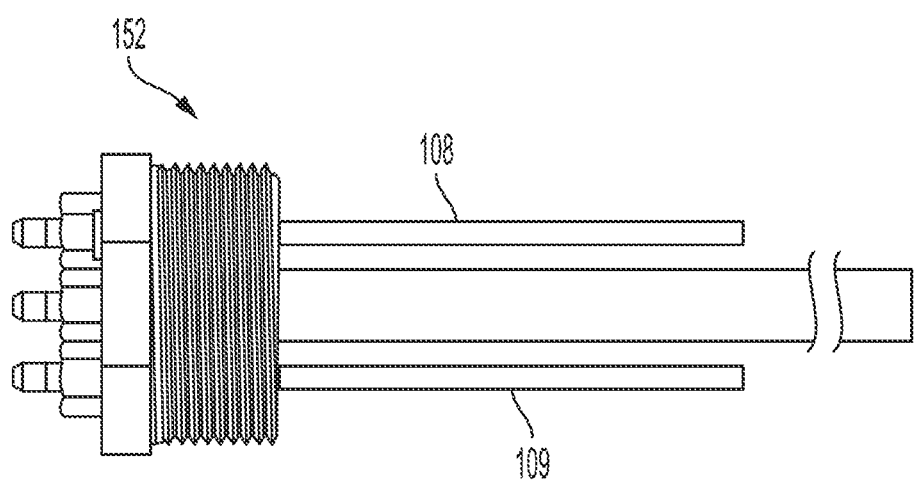
FIG. 6B illustrates a side view of the gas probe for use with the system, according to an example implementation.

FIG. 6A illustrates a perspective view of an example gas probe 152 for use with the system 100, according to an example implementation. FIG. 6B illustrates a side view of the gas probe 152 for use with the system 100, according to an example implementation. The gas probe 152 includes the temperature sensor 140, intake pathway 108 and return pathway 109. For installation of the system 100, in one example, the gas probe 152 is secured to the exhaust stack 120 to interface tubes/probes of the system 100 in a sealed manner. By integrating all of the sensing orifices and positions into a single unit, the gas probe 152 permits easy and rapid integration to a combustion system.

Figure 7:
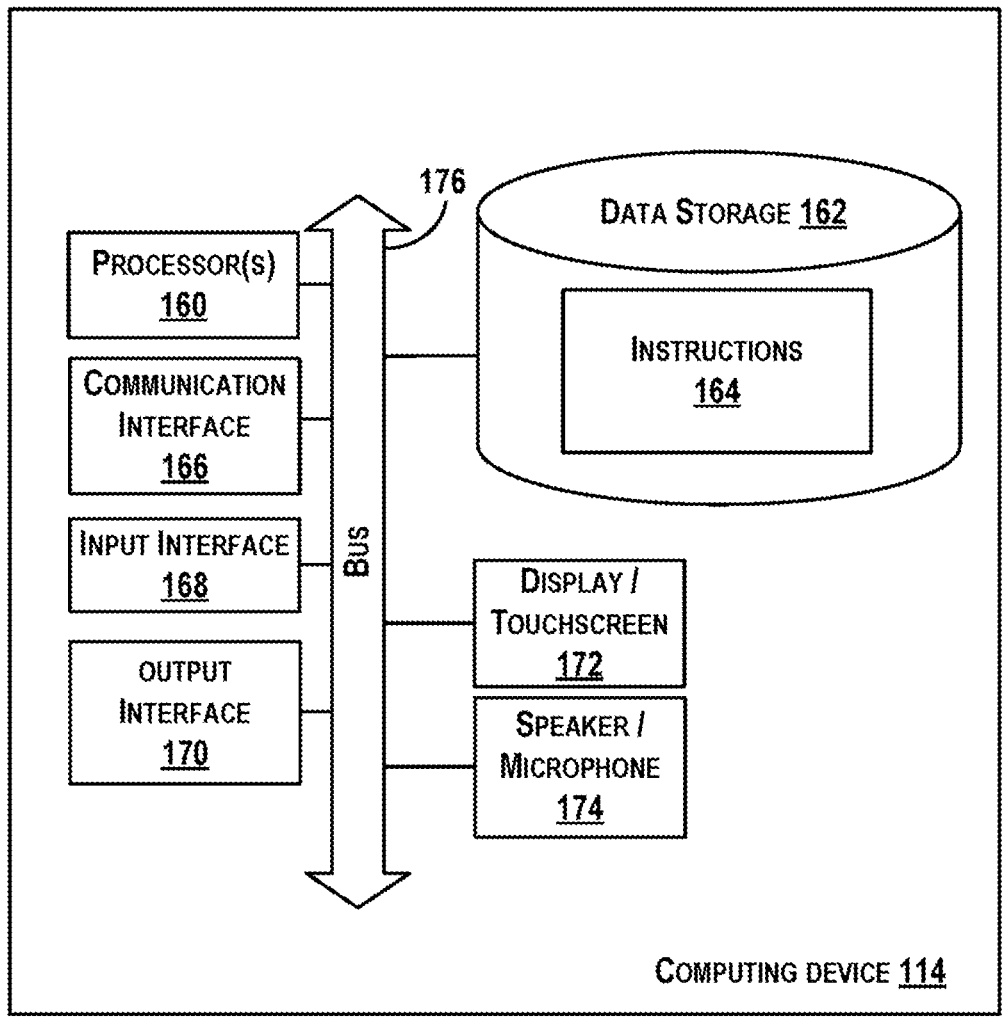
FIG. 7 illustrates a block diagram of the computing device, according to an example implementation.

FIG. 7 illustrates a block diagram of the computing device 114, according to an example implementation. FIG. 7 does not necessarily show all of the hardware and software modules included in the computing device 114, and omits physical and logical connections that will be apparent to one of ordinary skill in the art after review of the present disclosure.

The computing device 114 includes one or more processor(s) 160, and a non-transitory computer-readable media (data storage) 162 storing instructions 164, which when executed by the one or more processor(s) 160, causes the computing device 114 to perform functions (as described below). To perform functions, the computing device 114 includes a communication interface 166, an input interface 168, an output interface 170, and optionally includes a display/touchscreen 172 and a speaker/microphone 174, and each component of the computing device 114 is connected to a communication bus 176. The computing device 114 may also include hardware to enable communication within the computing device 114 and between the computing device 114 and other devices (not shown). The hardware may include transmitters, receivers, and antennas, for example.

The communication interface 166 is a wireless interface and/or one or more wireline interfaces that allow for both short-range communication and long-range communication to one or more networks or to one or more remote devices. Such wireless interfaces provide for communication under one or more wireless communication protocols, Bluetooth, WiFi (e.g., an institute of electrical and electronic engineers (IEEE) 802.11 protocol), Long-Term Evolution (LTE), cellular communications, near-field communication (NFC), and/or other wireless communication protocols. Such wireline interfaces include an Ethernet interface, a Universal Serial Bus (USB) interface, or similar interface to communicate via a wire, a twisted pair of wires, a coaxial cable, an optical link, a fiber-optic link, or other physical connection to a wireline network. Thus, the communication interface 166 is configured to receive input data from one or more devices, and configured to send output data to other devices.

In some examples, the communication interface 166 performs functions of the output interface 126 of the housing 104 shown in FIGS. 1-2 and FIG. 4, for example.

The data storage 162 includes or takes the form of memory, such as one or more computer-readable storage media that can be read or accessed by the one or more processor(s) 160. The computer-readable storage media includes volatile and/or non-volatile storage components, such as optical, magnetic, organic or other memory or disc storage, which can be integrated in whole or in part with the one or more processor(s) 160. The non-transitory data storage 162 is considered non-transitory computer readable media. In some examples, the non-transitory data storage 162 is implemented using a single physical device (e.g., one optical, magnetic, organic or other memory or disc storage unit), while in other examples, the non-transitory data storage 162 is implemented using two or more physical devices. The non-transitory data storage 162 thus is a computer readable medium, and instructions 164 are stored thereon. The instructions 164 include computer executable code.

The one or more processor(s) 160 include a general-purpose processor or special purpose processor (e.g., digital signal processors, application specific integrated circuits, etc.). The one or more processor(s) 160 receives inputs from the communication interface 166 as well as from other components (e.g., the display/touchscreen 162 or the speaker/microphone 164), and processes the inputs to generate outputs that are stored in the non-transitory data storage 162. The one or more processor(s) 160 are configured to execute the instructions 164 (e.g., computer-readable program instructions) that are stored in the non-transitory data storage 162 and are executable to provide the functionality of the computing device 114 described herein.

The input interface 168 is used to enter data or commands and can include, for example, a keyboard, a user pointing device such as, for example, a mouse, a trackball, or a touch pad, or may further include the touchscreen or microphone. In some examples, the input interface 166 performs functions of the user interface 146 of the housing 104 shown in FIG. 4, for example.

The output interface 170 outputs information for reporting or storage in the data storage 162, and thus, the output interface 170 may be similar to the communication interface 166 and can be a wireless interface (e.g., transmitter) or a wired interface as well.

Within one example, in operation, when the instructions 164 are executed by the one or more processor(s) 160, the one or more processor(s) 160 is caused to perform functions for detecting and tracking gas flow rate or flux and gas constituents of gas exiting the exhaust stack 120, such as resulting from combustion of natural gas, methane, coal, oil, or diesel fuel in a water heater, boiler, or heating and ventilation system within the building 102. In particular, the system 100 is configured to seat over or to connect to an outlet of the exhaust stack 120, track gas flow rate out of the exhaust stack 120, track concentrations of a set of gas constituents in gas exiting the exhaust stack 120 and therefore output by one or more utility systems servicing the building 102, and to transmit resulting data to the remote computer system 108. In one example, the remote computer system 108 is operable to then process the data through a machine learning-driven recommendation engine to identify total emissions from these utility systems (or from the building more generally) over a time period; derive a baseline emission condition for the building; characterize excess emissions from the building based on the baseline emissions condition; predict maintenance or adjustments to utility systems in the building to reduce emissions to the baseline emissions condition; compile these data into actionable insights; trigger alarms; and present these actionable insights to the building computer system 116 to guide emissions reduction and energy efficient improvement for the building.

Figure 8:
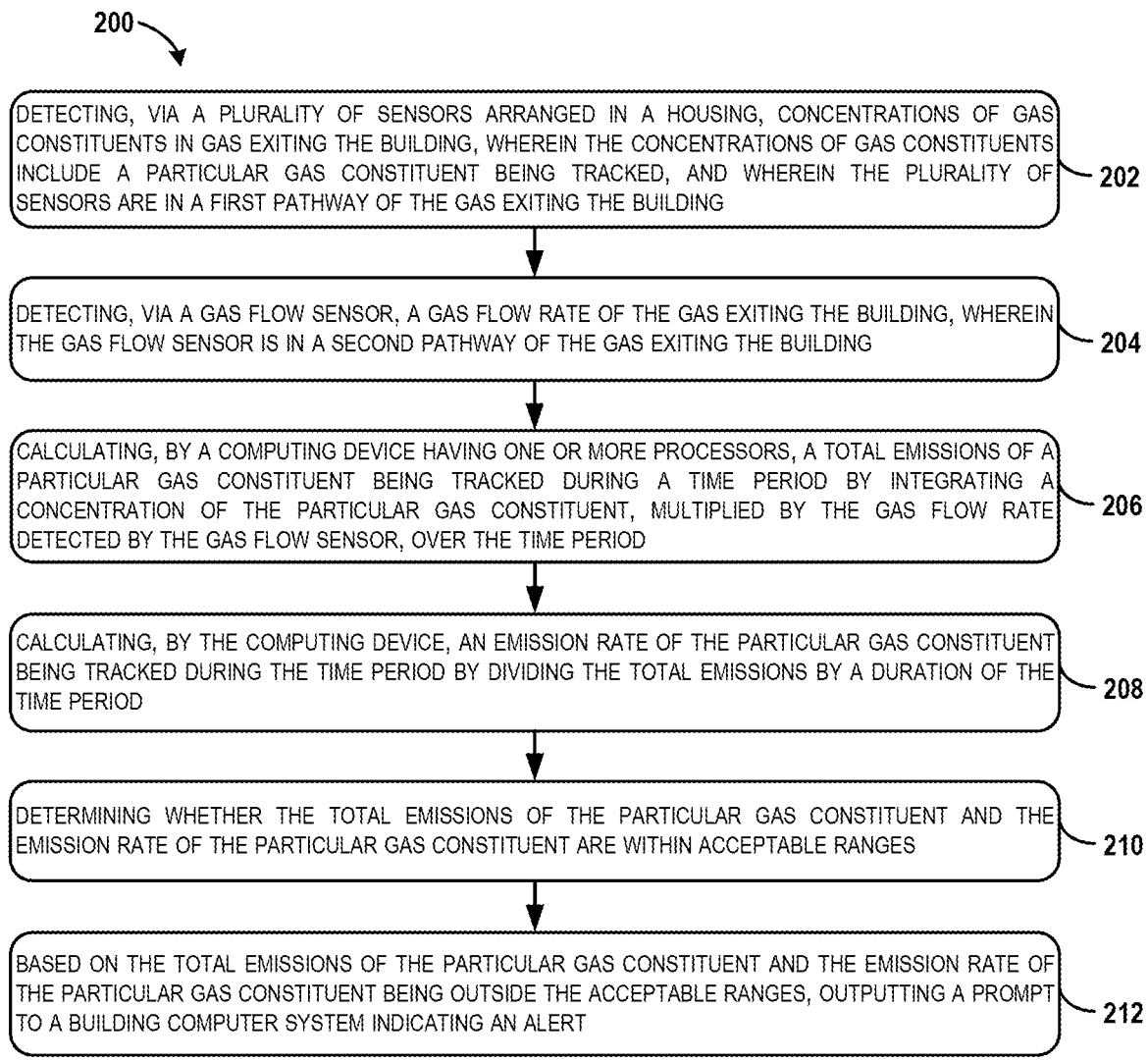
FIG. 8 is a flowchart illustrating an example of a method for measuring emissions from a building, according to an example implementation.

FIG. 8 is a flowchart illustrating an example of a method 200 for measuring emissions from a building, according to an example implementation. Method 200 shown in FIG. 8 presents an example of a method that could be used with or performed by the system 100 or the computing device 114 shown in the Figures herein, for example.

Within examples, devices or systems described herein are used or configured to perform logical functions presented in FIG. 8. In some instances, components of the devices and/or systems are configured to perform the functions such that the components are actually configured and structured (with hardware and/or software) to enable such performance. In other examples, components of the devices and/or systems are arranged to be adapted to, capable of, or suited for performing the functions, such as when operated in a specific manner. Method 200 includes one or more operations, functions, or actions as illustrated by one or more of blocks 202-212. Although the blocks are illustrated in a sequential order, these blocks may also be performed in parallel, and/or in a different order than those described herein. In addition, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, some blocks or portions of blocks may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium includes non-transitory computer readable medium or memory, for example, such as computer-readable media that stores data for short periods of time like register memory, processor cache and Random Access Memory (RAM). The computer readable medium additionally or alternatively includes non-transitory media, such as secondary or persistent long-term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block or portions of each block in FIG. 8, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 202, the method 200 includes detecting, via a plurality of sensors arranged in a housing, concentrations of gas constituents in gas exiting the building, and the concentrations of gas constituents include a particular gas constituent being tracked, and the plurality of sensors are in a first pathway of the gas exiting the building.

At block 204, the method 200 includes detecting, via a gas flow sensor, a gas flow rate of the gas exiting the building, and the gas flow sensor is in a second pathway of the gas exiting the building.

At block 206, the method 200 includes calculating, by a computing device having one or more processors, a total emissions of a particular gas constituent being tracked during a time period by integrating a concentration of the particular gas constituent, multiplied by the gas flow rate detected by the gas flow sensor, over the time period.

At block 208, the method 200 includes calculating, by the computing device, an emission rate of the particular gas constituent being tracked during the time period by dividing the total emissions by a duration of the time period.

At block 210, the method 200 includes determining (by the computing device) whether the total emissions of the particular gas constituent and the emission rate of the particular gas constituent are within acceptable ranges. For example, detection of natural gas (e.g., methane or CH4) above background levels of <5 ppm likely indicates a fault in a valve or incomplete combustion of the product and can be used as a threshold, so that an acceptable range for this gas constituent is 0-5 ppm or zero to about 5 ppm. In another example, higher than expected O2 levels (and/or CO level), such as >3% for natural gas, indicates that the fuel to air mixture is lean and therefore wasting both fuel and causing unnecessary emissions, so that an acceptable range for O2 in natural gas is 0-3% or zero to about 3%. In some examples, acceptable ranges are input by a user to the computing device per each gas constituent being monitored.

At block 212, the method 200 includes based on the total emissions of the particular gas constituent and the emission rate of the particular gas constituent being outside the acceptable ranges, outputting a prompt to a building computer system indicating an alert. The computing device can send a prompt, either wirelessly or via the network, to the building computer system.

Thus, in one example, the method 200 is executed to determine an emissions condition of the building. For instance, following deployment of the system 100 to the exhaust stack 120 on the building 102, the computing device 114 or the remote computer system 108 is operable to: track a concentration of a greenhouse gas (e.g., carbon dioxide) (e.g., in parts per million) exiting the exhaust stack 120 based on data output by a carbon dioxide sensor or the spectrometer; calculate total carbon dioxide emissions (e.g., in kilograms, tons) during a time period by integrating the concentration of carbon dioxide, multiplied by concurrent gas flow rate detected by the gas flow sensor, over this time period; calculate a carbon dioxide emission rate (e.g., tons per day) during the time period by dividing the total carbon dioxide emissions by a duration of the time period; and repeat this process for each other gas constituent tracked by the system 100. The source of gases and particulates may be from combustion, leakage, or incomplete processes.

As a result, where the concentrations of gas constituents comprises a plurality of gas constituents being tracked, the method 200 optionally includes repeating calculations of a total emissions for each of the plurality of gas constituents being tracked, and calculations of emission rates for each of the plurality of gas constituents being tracked, determining whether the total emissions of all of the plurality of gas constituents and the emission rates of all of the plurality of gas constituents are within acceptable ranges, and based on any of the total emissions of the plurality of gas constituents and the emission rates of the plurality of gas constituents being outside the acceptable ranges, outputting a prompt to a computer system indicating a utility modification to lessen an amount of one of the plurality of gas constituents.

In some examples, the computing device 114 executes these calculations locally and updates total emissions and emissions rates for these gas constituents after sampling the set of gas sensors and the gas flow sensor, such as at a rate of once per minute. Then, the computing device 114 intermittently uploads the derived total emissions and emissions rates to the remote computer system 108, such as once per day. In these examples, the computing device 114 is arranged in the housing 104, and the method 200 includes sampling the plurality of sensors 106a-d and the gas flow sensor 110 at a predetermined rate, executing calculations of the total emissions and the emission rate, and intermittently transmitting the total emission and the emission rate to the remote computer system 108 at a rate less than the predetermined rate.

In another example, the computing device 114 transmits raw gas constituent and gas flow data to a remote database or the remote computer system 108, such as by: streaming the data to the remote database in real-time or by aggregating and uploading the data (e.g., in a compressed data file) intermittently, such as once per day. The remote computer system 108 is operable to then retrieve the data from the remote database and derive total emissions and emissions rates for the building based on these data.

Baseline Emissions: Reduction in Secondary Gas Constituents

In some examples, the remote computer system 108 derives baseline gas constituent emissions from the exhaust stack 120 based on actual gas constituent emissions from the exhaust stack 120 and combustion characteristics derived from these actual gas constituent emissions. The baseline gas constituent emissions are used for comparisons as new data is captured, for example.

Generally, presence of secondary gas constituents (such as carbon monoxide, formaldehyde, nitrogen oxides, methane, and particulate) in exhaust emitted from the exhaust stack 120 may indicate: a dirty fuel source supplied to a utility system connected to the exhaust stack; wear in the utility system; and/or improper maintenance or tuning of the utility system. (These secondary gas constituents may also be more harmful (e.g., to humans or the environment) than carbon dioxide.) Fuel improvements, maintenance of the utility system, and/or replacement of the utility system may reduce or eliminate these second gas constituent emissions (and increase emissions of less-harmful carbon dioxide). Furthermore, fuel quality monitoring and/or utility system maintenance may represent basic, low-cost actions for building operations, though the user may be unaware of current fuel-related and utility system maintenance needs.

Therefore, the remote computer system 108 is operable to estimate carbon dioxide concentration from the exhaust stack 120 if fuel quality were improved and the utility system were tuned, such as based on: carbon monoxide, carbon dioxide, and formaldehyde concentrations detected in exhaust gas from the exhaust stack during the current sampling period; a chemical model as described below; and a nominal, mandated, or specified combustion efficiency of the utility system. The remote computer system 108 is operable to store this estimated carbon dioxide concentration as a baseline carbon dioxide concentration emitted from the exhaust stack during the sampling period (e.g., average ppm of carbon dioxide per day).

Additionally or alternatively, the remote computer system 108 is operable to calculate a baseline carbon dioxide emission from the exhaust stack per unit time (e.g., in kilograms or tons of carbon dioxide per day) during the current sampling period based on the baseline carbon dioxide concentration and the gas flow rate from the exhaust stack during the current sampling period. The remote computer system 108 can implement similar methods and techniques to calculate a baseline emissions of the secondary gas constituents from the exhaust stack per unit time (e.g., in kilograms or tons per day) during the current sampling period.

The remote computer system 108 is operable to then implement methods and techniques to: predict maintenance or tuning modes to reduce emissions of these secondary gas constituents; and serve a prompt to the user to service the utility system according to these maintenance or tuning modes in order to shift emissions of these secondary gas constituents down to these baseline values.

In these examples, the remote computer system 108 is operable to also: convert the amounts (e.g., weight, tons) of the secondary gas constituents emitted from the exhaust stack during the current sampling period into equivalent amounts of carbon dioxide emitted per unit time during the current sampling period; calculate difference between equivalent amounts of carbon dioxide and the baseline carbon dioxide emission per unit time; and present this difference to the user with the prompt to service the utility system in order to contextualize a predicted effect of servicing the utility system.

Thus, in some examples, the method 200 optionally includes estimating true energy consumption and true energy need for the building based on the concentrations of gas constituents and the gas flow rate detected, and outputting the true energy consumption and the true energy need for the building to the building computer system.

In further examples, the method 200 optionally includes deriving a baseline emission condition for the utility system based on the total emissions of the particular gas constituent being tracked that has been calculated, and based on the total emissions of the particular gas constituent increasing over time, determining one or more adjustments to the utility system of the building to reduce the total emissions to the baseline emission condition.

Baseline Emissions: Chemical Model and Thermal Need

In a similar implementation, the remote computer system 108 calculates a baseline carbon dioxide emission from the exhaust stack per unit time (e.g., in kilograms, tons of carbon dioxide per day) during the current sampling period, based on predicted changes in carbon dioxide concentration given possible reduction (or elimination) of the secondary gas constituents from exhaust stack emissions that may result from utility system maintenance, and based on reduced fuel consumption for the same output that may result from utility system maintenance that reduces secondary gas constituent emissions.

For example, the remote computer system is operable to estimate a fuel type for the utility system based on gas constituents, such as: methane if methane is present in the gas constituents; coal if high particulate content is present in the gas constituents; oil if nitrogen oxide is present in high concentration the gas constituents; or natural gas or liquid petroleum if formaldehyde is present in high concentration the gas constituents. Alternatively, the remote computer system is operable to retrieve the fuel type for the utility system from the building profile—associated with the building—described above.

The remote computer system is operable to then retrieve a chemical model that characterizes conversion of the fuel type into the gas constituents and thermal output units (or "therms") under a range of combustion efficiencies and/or combustion conditions. Accordingly, the remote computer system can insert the total amount of the gas constituents detected (e.g., gas constituent concentrations multiplied by the total gas flux from the exhaust stack) during the current sampling period into the chemical model to estimate: a total amount of the fuel type consumed during the sample period; total therms converted from the fuel type during the sampling period (which represents a nominal thermal need during the current sampling period); and/or a combustion efficiency of the utility system during the sampling period.

A number of chemical models exist for use. In one example, a combustion efficiency model is used. For instance, methane, when combusted properly, should result in approximately 3% O2 in the exhaust stream and any amounts lower than this is running a rich air to fuel ratio (and risking detonation), whereas higher amounts than this results in a lean air to fuel ratio.

The remote computer system is operable to also retrieve a nominal combustion efficiency of the utility system, such as from: settings of a local municipality; stored in the building profile; set by the user; retrieved or extracted from a manufacturer specification for the utility system; or characteristic of well-maintained utility systems of similar types and ages as the utility system in the building. The remote computer system is operable to then: estimate a baseline amount of the fuel (e.g., in kilograms, tons) to yield the total output therms given nominal combustion efficiency in the utility system during the sampling period based on the chemical model; and estimate baseline amounts of gas constituent emission from the exhaust stack during the sampling period based on the chemical model, the baseline amount of the fuel, and the nominal combustion efficiency. Based on the duration of the sampling period, the computer system is operable to also: convert these baseline amounts of gas constituent emission into baseline gas constituent emissions per unit time; and similarly convert the baseline amount of the fuel into a baseline fuel consumption per unit time.

Therefore, the remote computer system is operable to calculate and store baseline fuel consumption and baseline total gas constituent emissions from the exhaust stack per unit time based on: a nominal (e.g., target, accessible, required) combustion efficiency for the utility system; and nominal thermal need from the utility system during the current sampling period.

More specifically, in this implementation, the remote computer system is operable to derive baseline gas constituent emissions from the exhaust stack per unit time based on a predicted distribution of gas constituents emitted from the exhaust stack if the connected utility system(s) operated at a combustion efficiency and output similar amount of thermal energy during the current sampling period.

In this implementation, the remote computer system is operable to also: convert the amounts (e.g., weight, tons) of the secondary gas constituents emitted from the exhaust stack during the current sampling period into equivalent amounts of carbon dioxide emitted per unit time during the current sampling period; calculate a total effective carbon dioxide emission per unit time from the exhaust stack based on these equivalent amounts of carbon dioxide and the total carbon dioxide emission during the sampling period; calculate a difference between total effective carbon dioxide emission per unit time and the baseline carbon dioxide emission per unit time; and present this difference to the user with the prompt to service the utility system in order to contextualize a predicted effect of servicing the utility system.

Additionally or alternatively, the remote computer system is operable to: retrieve a current fuel price for the fuel type consumed by the utility system; calculate a predicted reduction in fuel consumption per unit time based on the actual amount of fuel consumed during sampling period and the baseline amount of the fuel per unit time; calculate a reduction in fuel cost per unit time based on the current fuel price and the predicted reduction in fuel consumption per unit time; and present this reduction in fuel cost per unit time to the user with the prompt to service the utility system in order to further contextualize the predicted effect of servicing the utility system.

Additionally or alternatively, the remote computer system is operable to: retrieve current or expected future weather conditions and either retune the combustion device directly or inform an operator that efficiencies can be improved.

Baseline Emissions: Energy Consumption

In the foregoing implementation, the remote computer system 108 retrieves building characteristics (such as building type, size (e.g., square footage), age, and/or average occupancy) from the building profile. The remote computer system 108 then: retrieves baseline fuel (or energy) consumption per unit time and per square foot or per occupant for buildings of the same or similar characteristics from accessible databases via the network 127; calculates a baseline total fuel consumption from the building per unit time based on characteristics of the building and the baseline fuel consumption per unit time; and implements the chemical model described above to calculate baseline gas constituent emissions per unit time from the building—given the nominal combustion efficiency of utility systems in the building and fuel types of the utility systems—based on the baseline total fuel consumption from the building per unit time.

In this implementation, the remote computer system is operable to: convert the amounts (e.g., weight, tons) of the secondary gas constituents emitted from the building during the current sampling period into equivalent amounts of carbon dioxide emitted per unit time during the current sampling period; and calculate a total effective carbon dioxide emission per unit time from the building based on these equivalent amounts of carbon dioxide and the total carbon dioxide emission during the sampling period.

Similarly, the remote computer system is operable to: convert the baseline gas constituent emissions per unit time from the building into equivalent amounts of carbon dioxide emitted per unit time; and calculate a total baseline effective carbon dioxide emission per unit time for the building based on these equivalent amounts of carbon dioxide and the baseline carbon dioxide emission per unit time. The remote computer system is operable to then: calculate a difference between total effective carbon dioxide emission per unit time and the total baseline carbon dioxide emission per unit time; and present this difference to the user with the prompt to service the utility system in order to contextualize a predicted effect of servicing the utility system and bring fuel consumption in line with similar buildings.

The remote computer system also is operable to: retrieve a current fuel price for the fuel type consumed by the utility system; calculate a predicted reduction in fuel consumption per unit time based on the actual amount of fuel consumed by the utility system during the sampling period and the baseline amount of the fuel per unit time; calculate a reduction in fuel cost per unit time based on the current fuel price and the predicted reduction in fuel consumption per unit time; and present this reduction in fuel cost per unit time to the user with the prompt to service the utility system in order to further contextualize the predicted effect of servicing the utility system.

In some examples, in which the building includes multiple exhaust stacks, each connected to one or more utility systems, one instance of the system 100 is operable to be installed on each exhaust stack on the building and can independently collect and return gas constituent and gas flow rate data to the remote computer system. For example, the building can include multiple boilers and HVAC units, such as serving different wings or floors of the building. In this example, the computer system is operable to: derive total emissions, gas constituent emission rates, baseline gas constituent emissions, and/or baseline fuel consumption, etc. from each exhaust stack; and interpret operating conditions, maintenance needs, and replacement opportunities for utility systems connected to these exhaust stacks based on data collected by these instances of the system.

Furthermore, the remote computer system is operable to rank or prioritize these operating conditions, maintenance needs, and replacement opportunities and selectively prompt the user to take action within the building accordingly. For example, the remote computer system is operable to rank maintenance needs for utility systems in the building: proportional to concentration of formaldehyde or emissions rate (e.g., kilograms per day) of formaldehyde; proportional to a difference between actual and baseline effective carbon dioxide emissions rates; or proportional to a difference between actual and baseline fuel consumption rates; etc. The remote computer system then selectively prompts the user to implement the highest-priority maintenance action.

In this variation, the remote computer system is operable to also aggregate baseline fuel consumption and baseline gas constituent emissions per unit time from these exhaust stacks into a baseline total fuel consumption and baseline total gas constituent emissions per unit time from the building.

Maintenance Predictions

In some examples, the remote computer system 108 uses detected concentrations of gas constituents and gas flow rate to predict deficient operation and possible correction modes for a utility system connected to the exhaust stack based on gas constituent concentrations detected by the system. In one implementation, the computer system retrieves and navigates through a predefined decision tree to identify maintenance and replacement actions for the utility system.

For example, in response to detecting a high nitrogen oxide concentration within the concentrations of gas constituents in gas exiting the exhaust stack that are detected, the remote computer system 108 identifies a lean combustion condition in the utility equipment 118, predicts a need to clean the utility equipment 118, and outputs the prompt to the computer system 116 indicating a need to clean the utility equipment 118 to increase a fuel-to-air ratio of the utility system. An example of a high nitrogen oxide concentration includes an amount over a threshold, such as 50 ppb (parts per billion).

In another example, in response to detecting a formaldehyde concentration above a trace amount (e.g., >5 ppb) within the concentrations of gas constituents in gas exiting the exhaust stack that are detected, the remote computer system 108 predicts a need to service the system, such as cleaning the pilot lights or adjust a fuel-to-air ratio of the utility system due to incomplete combustion; and generates and sends a prompt to the computer system 116 indicating a need to adjust a fuel-to-air ratio of the utility system due to incomplete combustion.

In another example, in response to detecting a methane concentration above a trace amount (e.g., >5 ppm) within the concentrations of gas constituents in gas exiting the exhaust stack that are detected, the remote computer system 108 predicts a methane leak or incorrect fuel-to-air ratio of the utility system, and generates and sends a prompt to the building computer system 116 to inspect the utility system and indicating a methane leak or incorrect fuel-to-air ratio of the utility system has been detected.

In another example, in response to detecting a nitrogen oxide concentration above a threshold (e.g., above 50 ppb) continuous over an extended period of time (e.g., twelve hours, two days) within the concentrations of gas constituents in gas exiting the exhaust stack that are detected, the remote computer system 108 identifies the utility system as always on or running at high load, which is correlated with increased nitrogen oxide generation; predicts that the utility system is undersized for its application; and generates and sends a prompt to the building computer system 116 indicating that the utility system is running at high load and is undersized for the building.

Similarly, in response to detecting frequent increases followed by decreases in methane and formaldehyde concentrations over an extended period of time (e.g., repeating on twenty-minute intervals) within the concentrations of gas constituents in gas exiting the exhaust stack that are detected, the remote computer system identifies the utility system as frequently cycling on and off; predicts that the utility system is oversized for its application; and generates and sends a prompt to the building computer system 116 indicating that the utility system is cycling on and off and is oversized for the building.

In another implementation, in response to detecting out of range concentrations of secondary gas constituents (e.g., thousands of ppm of carbon monoxide, methane, nitrogen oxide, sulfur oxide, formaldehyde) within the concentrations of gas constituents in gas exiting the exhaust stack that are detected, such as above preset threshold levels, the remote computer system 108 predicts that the utility system is in need of maintenance; and generates and sends a prompt to the building computer system 116 indicating to replace the utility system.

Many examples described herein are in relation to an exhaust stack coupled to a boiler or water heater, for example. In alternate implementations, the gas exiting the building exits from an exhaust stack coupled to an air conditioning utility system of the building. For such different types of utility systems, methods for monitoring emissions include detecting, either direct emissions from refrigerant leakage or a temperature of components of the air conditioning utility system (e.g., across a compressor and coil), and determining, by the computing device, an efficiency of the air conditioning utility system based on a difference in the temperature of components of the air conditioning utility system. As such, based on the efficiency of the air conditioning utility system being less than a threshold, the computing device outputs the prompt to the building computing system indicating a possible refrigerant leak.

Thus, other greenhouse gas emissions that may not occur as part of a byproduct of combustion (for example, refrigerant losses) are capable of being monitored using the system 100 herein. In one example, non-combustion emissions (such as refrigerant losses or leaks of an air conditioner) can be monitored and discovered by the system when used independently from any combustion measurements, e.g., in a heat pump, air conditioning unit, or some other system that does not combust fossil fuels directly.

Additionally or alternatively, the remote computer system can implement artificial intelligence, machine learning, and/or any other methods or techniques to interpret operating conditions, maintenance needs, and replacement opportunities of a utility system connected to an exhaust stack on a building based on gas constituent data collected by the system.

Figure 9:
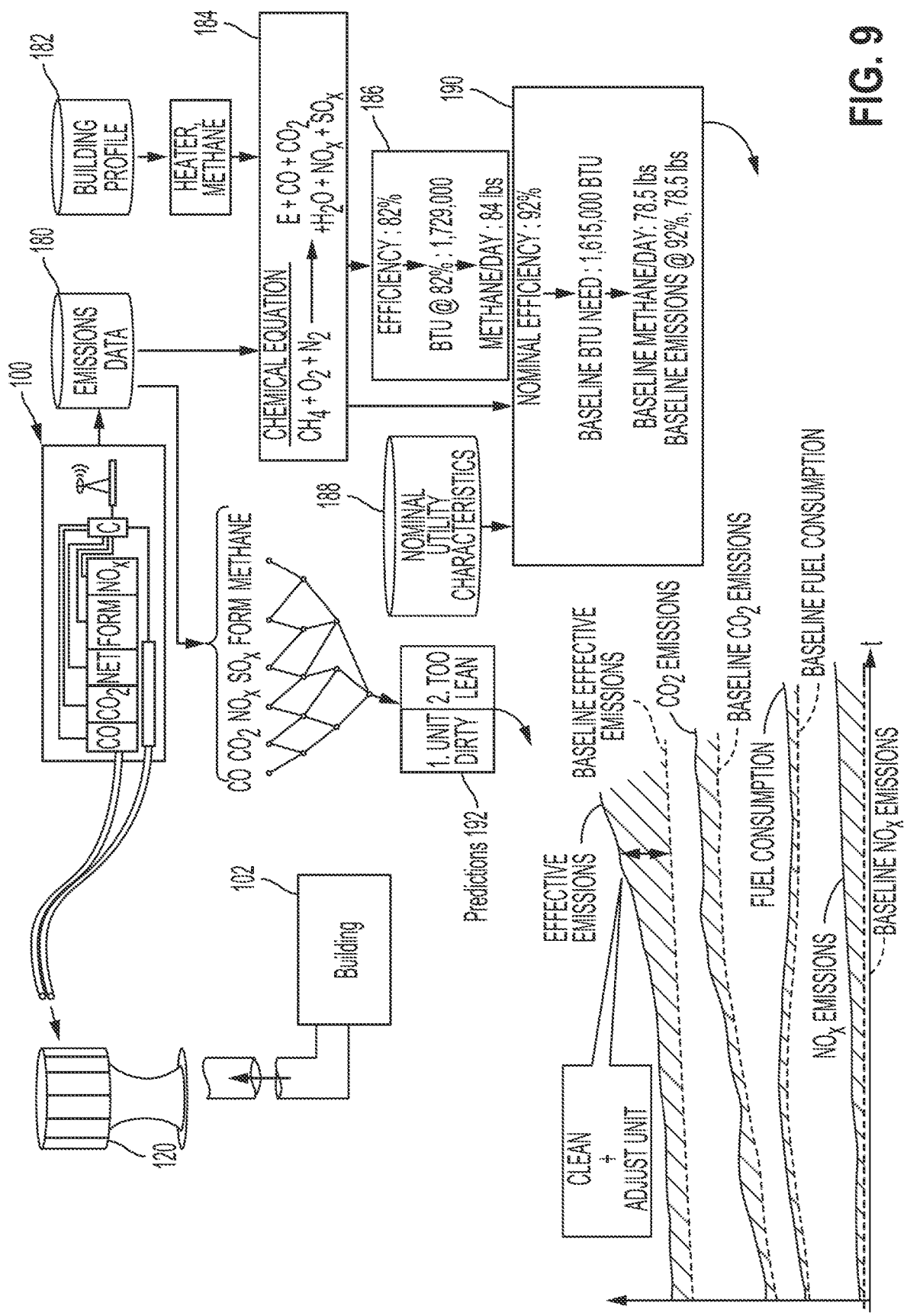
FIG. 9 is a process flow diagram illustrating an example usage of the system 100, according to an example implementation.

FIG. 9 is a process flow diagram illustrating an example usage of the system 100, according to an example implementation. Outputs of the system 100 are shown as emissions data 180, which can be stored locally by the computing device 114 and/or transmitted to the remote computer system 108. In combination with a building profile 182, a chemical model 184 is used to determine efficiency calculations 186 of the utility equipment of the building 102, for example.

In addition, using nominal utility characteristics 188, comparisons can be made with the efficiency calculations 186 to provide an analysis 190 of the utility system in the building. The analysis 190 can be provided in a form of data or graphs, as shown, illustrating trends over time, for example.

In further examples, the emissions data 180 is analyzed, as described above, to generate predictions 192, such as any of the predictions described above.

Visualizations

Figure 10:
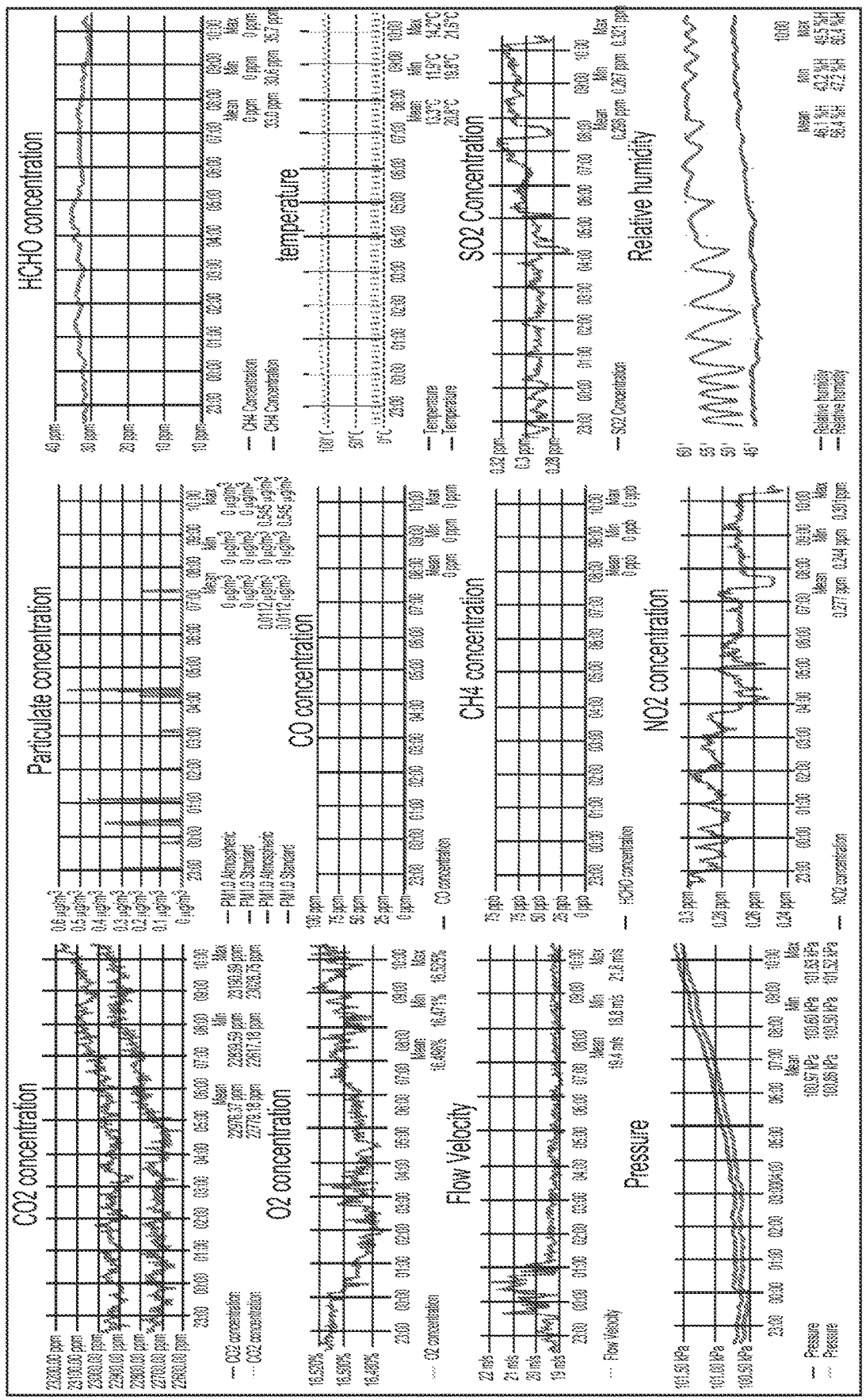
FIG. 10 is an example graphical user interface showing graphs of data collected by the system, according to an example implementation.

Within examples, the remote computer system 108 compiles actual gas constituent emissions, actual gas flow rate, baseline gas constituent emissions, and/or other data described above into a visualization and presents this visualization to the user via the operator portal. FIG. 10 is an example graphical user interface showing graphs of data collected by the system, according to an example implementation. For example, FIG. 10 includes graphs of data representative of CO2 concentration, O2 concentration, flow velocity, pressure, particulate concentration, CO concentration, CH4 concentration, NO2 concentration, HCHO concentration, temperature, SO2 concentration, and relative humidity.

Figure 11:
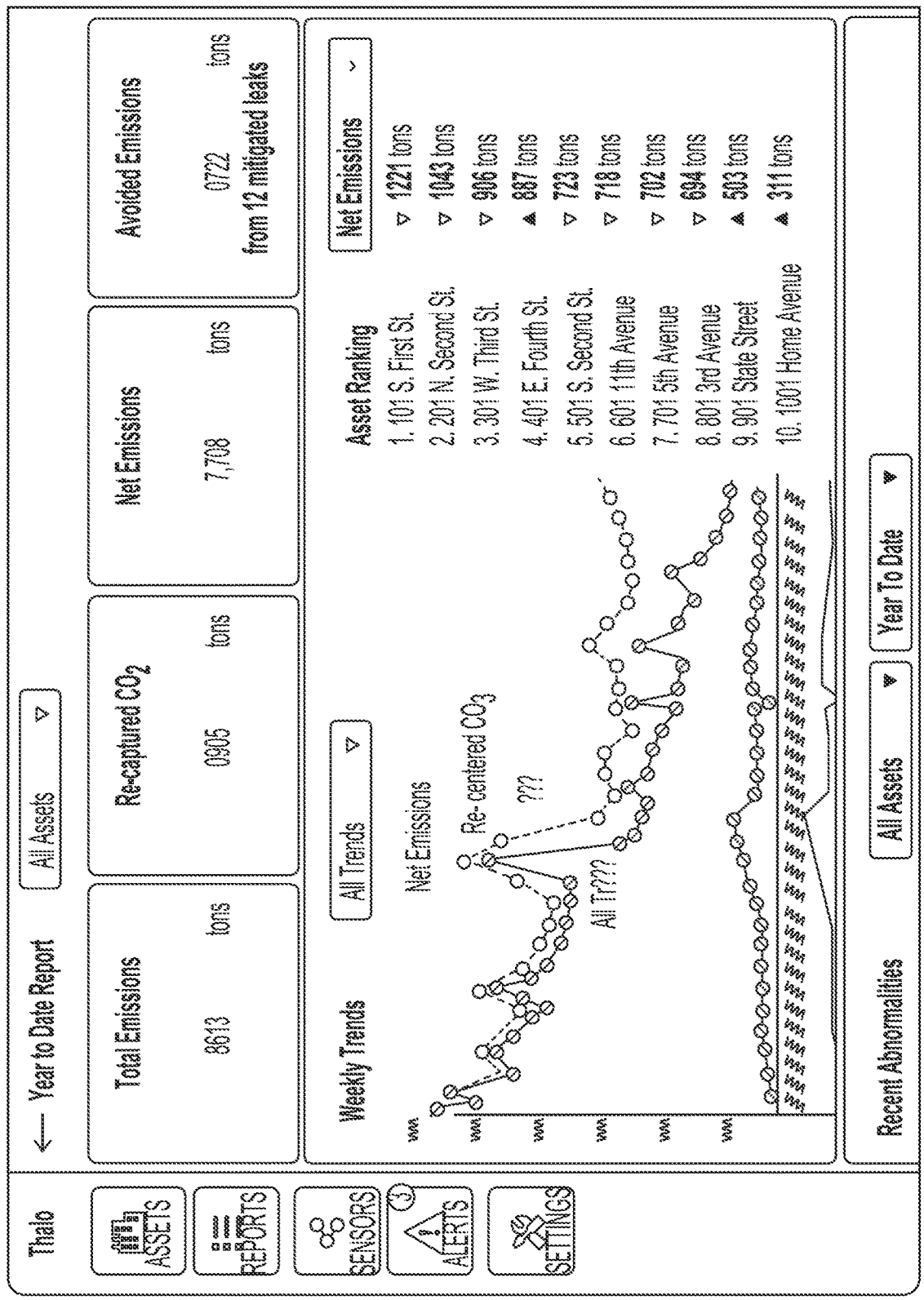
FIG. 11 is another example graphical user interface showing data collected by the system summarizing multiple timespans and multiple buildings, according to an example implementation.

FIG. 11 is another example graphical user interface showing data collected by the system 100, according to an example implementation. In this implementation, the remote computer system initializes a chart representing emissions quantity (e.g., in kilograms, tons) versus time and populates the chart with: total gas constituent emissions per day for a period of time (e.g., two weeks); baseline gas constituent emissions per day; effective carbon dioxide emissions per day for this period of time; and baseline effective carbon dioxide emissions per day for the building or a particular exhaust stack on the building. The remote computer system can also: highlight greatest differences between actual and baseline emissions for particular gas constituents or effective carbon dioxide emissions; and annotate the difference with a call to action (e.g., utility system maintenance or replacement) as described above. The remote computer system can then serve this visualization to the user via the operator portal.

Furthermore, the remote computer system can: retrieve an emissions factor based on characteristics of the building, such as stored in the building profile; retrieve energy consumption logs for the building; convert the emissions factor and energy consumption data into nominal emissions conditions per day for the building; populate the chart with these nominal emissions conditions; calculate a total quantity of recaptured carbon dioxide emissions over the period of time and/or a total quantity of recaptured carbon dioxide emissions per day based on differences between these nominal and actual emissions conditions; and present these total quantity of recaptured carbon dioxide emission values on or adjacent the chart.

Additionally or alternatively, the remote computer system can initialize a chart representing emissions rate (e.g., weight per unit time) versus time and populate this chart with: total gas constituent emission rate per day for a period of time (e.g., two weeks); baseline gas constituent emission rates per day; effective carbon dioxide emission rate per day for this period of time; and baseline effective carbon dioxide emission rate per day for the building or a particular exhaust stack on the building. The remote computer system can: highlight greatest differences between actual and baseline emission rates for particular gas constituents or effective carbon dioxide emissions; and annotate this difference with a call to action (e.g., utility system maintenance or replacement) as described above.

However, the remote computer system can implement any other method or technique to aggregate actual detected emissions, derived baseline emissions data, and calls to action related to utility systems connected to exhaust stacks monitored by instances of the system deployed to the building.

The remote computer system and instances of the system can similarly cooperate: to monitor emissions from multiple buildings (e.g., all managed by the user); to derive baseline emission characteristics for the buildings based on data collected by these instances of the system; to derive calls to action for utility systems in these buildings; and to prioritize distribution of these calls to action to the user over time.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or any sub-combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples describe different advantages as compared to other advantageous examples. The example or examples selected are chosen and described to explain the principles of the examples, the practical application, and to enable others of ordinary skill in the art to understand the disclosure for various examples with various modifications as are suited to the particular use contemplated.

Having described the subject matter of the present disclosure in detail and by reference to specific examples thereof, it is noted that the various details disclosed herein should not be taken to imply that these details relate to elements that are essential components of the various examples described herein, even in cases where a particular element is illustrated in each of the drawings that accompany the present description. Further, it will be apparent that modifications and variations are possible without departing from the scope of the present disclosure, including, but not limited to, examples defined in the appended claims. More specifically, although some aspects of the present disclosure are identified herein as preferred or particularly advantageous, it is contemplated that the present disclosure is not necessarily limited to these aspects.

Moreover, while some examples have been described in the context of fully functioning computers and computer systems, those skilled in the art will appreciate that various examples are capable of being distributed as a program product in a variety of forms, and that the disclosure applies equally regardless of a particular type of machine or computer-readable media used to effect the distribution.

Further examples of machine-readable storage media, machine-readable media, or computer-readable (storage) media include, but are not limited to, recordable type media such as volatile and non-volatile memory devices, floppy and other removable drives, hard drives, optical disks (e.g., Compact Disk Read-Only Memory (CD ROMS), Digital Versatile Disks, (DVDs), etc.), among others, and transmission type media such as digital and analog communication links.

For the purposes of describing and defining examples herein, it is noted that terms "substantially" or "about" are utilized herein to represent an inherent degree of uncertainty attributed to any quantitative comparison, value, measurement, or other representation. The terms "substantially" and "about," when utilized herein, represent the degree by which a quantitative representation may vary from a stated reference without resulting in a change in a basic function of the subject matter at issue, such as varying by 0-2% of the quantitative measurement.

What is claimed is:

1. A system for measuring emissions from a building, comprising:
   a housing;
   a plurality of sensors arranged in the housing to detect concentrations of gas constituents in gas exiting the building, wherein the concentrations of gas constituents include a particular gas constituent being tracked, and wherein the plurality of sensors are in a first pathway of the gas exiting the building;
   a gas flow sensor to detect a gas flow rate of the gas exiting the building, wherein the gas flow sensor is in a second pathway of the gas exiting the building;
   a computing device having one or more processors, to perform functions comprising:
      calculating a total emissions of the particular gas constituent being tracked during a time period by integrating a concentration of the particular gas constituent detected by the plurality of sensors, multiplied by the gas flow rate detected by the gas flow sensor, over the time period;
      calculating an emission rate of the particular gas constituent being tracking during the time period by dividing the total emissions by a duration of the time period;
      determining whether the total emissions of the particular gas constituent and the emission rate of the particular gas constituent are within acceptable ranges; and
      based on the total emissions of the particular gas constituent and the emission rate of the particular gas constituent being outside the acceptable ranges, outputting a prompt to a building computer system indicating an alert.

2. The system of claim 1, wherein the computing device is arranged in the housing, and the functions further comprise:
   sampling the plurality of sensors and the gas flow sensor at a predetermined rate;
   executing said calculating of the total emissions and the emission rate; and
   intermittently transmitting the total emission and the emission rate to a remote computer system at a rate less than the predetermined rate.

3. The system of claim 1, wherein the computing device is located separate from the housing, and the housing comprises a wireless communication transmitter to transmit outputs of the plurality of sensors and the gas flow sensor to the computing device.

4. The system of claim 1, wherein the plurality of sensors include gas sensors to detect concentrations of gas constituents comprising carbon dioxide, carbon monoxide, particulate matter, sulfur oxide, nitrogen, methane, oxygen, and formaldehyde.

5. The system of claim 1, wherein the plurality of sensors further comprise a temperature sensor, a humidity sensor, and a pressure sensor.

6. The system of claim 1, wherein the plurality of sensors include a spectrometer to detect the concentrations of the gas constituents in the gas exiting the building based on an intensity of detected light.

7. The system of claim 1, wherein the housing is configured to seat over an exhaust stack of the building, and wherein the gas flow sensor is arranged in the housing.

8. The system of claim 7, wherein the housing includes a set of perforations configured to pass the gas exiting the exhaust stack, and wherein the plurality of sensors and the gas flow sensor are positioned proximal to the perforations such that the plurality of sensors and the gas flow sensor are in a pathway of the gas exiting the exhaust stack.

9. The system of claim 1, further comprising:
 a sampling tube fluidly coupled to the plurality of sensors and extending from the housing and into an exhaust stack of the building.

10. The system of claim 9, wherein the gas flow sensor is coupled to a distal end of the sampling tube and the distal end of the sampling tube is inserted into the exhaust stack, wherein the second pathway comprises the sampling tube.

11. The system of claim 1, further comprising:
 an intake into which an input stream of a portion of the gas exiting the building passes; and
 an intake sensor for conditioning the input stream prior to the input stream passing through the first pathway.

12. The system of claim 11, wherein the intake sensor is selected from the group consisting of a dehumidifying sensor, a heater, a cooling device, a particulate filter, and a gas filter.

13. A method for measuring emissions from a building, comprising:
 detecting, via a plurality of sensors arranged in a housing, concentrations of gas constituents in gas exiting the building, wherein the concentrations of gas constituents include a particular gas constituent being tracked, and wherein the plurality of sensors are in a first pathway of the gas exiting the building;
 detecting, via a gas flow sensor, a gas flow rate of the gas exiting the building, wherein the gas flow sensor is in a second pathway of the gas exiting the building;
 calculating, by a computing device having one or more processors, a total emissions of a particular gas constituent being tracked during a time period by integrating a concentration of the particular gas constituent, multiplied by the gas flow rate detected by the gas flow sensor, over the time period;
 calculating, by the computing device, an emission rate of the particular gas constituent being tracked during the time period by dividing the total emissions by a duration of the time period;
 determining whether the total emissions of the particular gas constituent and the emission rate of the particular gas constituent are within acceptable ranges; and
 based on the total emissions of the particular gas constituent and the emission rate of the particular gas constituent being outside the acceptable ranges, outputting a prompt to a building computer system indicating an alert.

14. The method of claim 13, wherein the concentrations of gas constituents comprises a plurality of gas constituents being tracked, and the method further comprises:
 repeating said calculating of a total emissions for each of the plurality of gas constituents being tracked, and said calculating of emission rates for each of the plurality of gas constituents being tracked;
 determining whether the total emissions of all of the plurality of gas constituents and the emission rates of all of the plurality of gas constituents are within acceptable ranges; and
 based on any of the total emissions of the plurality of gas constituents and the emission rates of the plurality of gas constituents being outside the acceptable ranges, outputting a prompt to a computer system indicating a utility modification to lessen an amount of one of the plurality of gas constituents.

15. The method of claim 13, wherein the computing device is arranged in the housing, and the method further comprises:
 sampling the plurality of sensors and the gas flow sensor at a predetermined rate;
 executing said calculating of the total emissions and the emission rate; and
 intermittently transmitting the total emission and the emission rate to a remote computer system at a rate less than the predetermined rate.

16. The method of claim 13, wherein the computing device is located separate from the housing and wherein the housing comprises a wireless communication transmitter, and the method further comprises:
 transmitting outputs of the plurality of sensors and the gas flow sensor to the computing device.

17. The method of claim 13, further comprising:
 estimating true energy consumption and true energy need for the building based on the concentrations of gas constituents and the gas flow rate detected; and
 outputting the true energy consumption and the true energy need for the building to the building computer system.

18. The method of claim 13, wherein the gas exiting the building exits from an exhaust stack coupled to a utility system of the building, and the method further comprises:
 deriving a baseline emission condition for the utility system based on the total emissions of the particular gas constituent being tracked that has been calculated; and
 based on the total emissions of the particular gas constituent increasing over time, determining one or more adjustments to the utility system of the building to reduce the total emissions to the baseline emission condition.

19. The method of claim 13, wherein the gas exiting the building exits from an exhaust stack coupled to a utility system of the building, and the method further comprises:
 in response to detecting a nitrogen oxide concentration above a threshold concentration within the concentrations of gas constituents in gas exiting the exhaust stack that are detected, outputting the prompt to the computer system indicating a need to clean the utility system and increase a fuel-to-air ratio of the utility system.

20. The method of claim 13, wherein the gas exiting the building exits from an exhaust stack coupled to a utility system of the building, and the method further comprises:
 in response to detecting a nitrogen oxide concentration above a threshold concentration continuous over an extended period of time within the concentrations of gas constituents in gas exiting the exhaust stack that are detected, outputting the prompt to the computer system indicating that the utility system is running at high load and is undersized for the building.

21. The method of claim 13, wherein the gas exiting the building exits from an exhaust stack coupled to a utility system of the building, and the method further comprises:
in response to detecting a formaldehyde concentration above a trace amount within the concentrations of gas constituents in gas exiting the exhaust stack that are detected, outputting the prompt to the computer system indicating a need to adjust a fuel-to-air ratio of the utility system due to incomplete combustion.

22. The method of claim 13, wherein the gas exiting the building exits from an exhaust stack coupled to a utility system of the building, and the method further comprises:
in response to detecting a methane concentration above a trace amount within the concentrations of gas constituents in gas exiting the exhaust stack that are detected, outputting the prompt to the computer system indicating a methane leak or incorrect fuel-to-air ratio of the utility system.

23. The method of claim 13, wherein the gas exiting the building exits from an exhaust stack coupled to a utility system of the building, and the method further comprises:
in response to detecting increases followed by decreases in methane and formaldehyde concentrations over a period of time within the concentrations of gas constituents in gas exiting the exhaust stack that are detected, outputting the prompt to the computer system indicating that the utility system is cycling on and off and is oversized for the building.

24. The method of claim 13, wherein the gas exiting the building exits from an exhaust stack coupled to a utility system of the building, and the method further comprises:
in response to detecting out of range concentrations of secondary gas constituents within the concentrations of gas constituents in gas exiting the exhaust stack that are detected, outputting the prompt to the computer system indicating that the utility system requires maintenance.

25. The method of claim 13, wherein the gas exiting the building exits from an exhaust stack coupled to an air conditioning utility system of the building, and the method further comprises:
detecting a temperature of components of the air conditioning utility system;
determining, by the computing device, an efficiency of the air conditioning utility system based on a difference in the temperature of components of the air conditioning utility system; and
based on the efficiency of the air conditioning utility system being less than a threshold, outputting the prompt to the building computing system indicating a possible refrigerant leak.

* * * * *